United States Patent
Tanaka et al.

(10) Patent No.: US 6,683,207 B2
(45) Date of Patent: Jan. 27, 2004

(54) PRODUCTION METHOD OF (R)-3 HYDROXY-3-(2-PHENYLETHYL) HEXANOIC ACID AND INTERMEDIATE THEREOF

(75) Inventors: Masahide Tanaka, Osaka (JP); Kozo Matsui, Osaka (JP); Tadashi Katsura, Osaka (JP); Mitsuhiro Iwasaki, Osaka (JP); Hiroshi Maeda, Osaka (JP); Nobushige Itaya, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 10/320,325

(22) Filed: Dec. 16, 2002

(65) Prior Publication Data

US 2003/0176507 A1 Sep. 18, 2003

(30) Foreign Application Priority Data

Feb. 7, 2002 (JP) ........................ 2002-030724
Feb. 19, 2002 (JP) ........................ 2002-041480
Apr. 8, 2002 (JP) ........................ 2002-105772

(51) Int. Cl.$^7$ .............................................. C07C 59/48
(52) U.S. Cl. ...................................... 562/470; 562/401
(58) Field of Search ................................ 562/470, 401

(56) References Cited

U.S. PATENT DOCUMENTS

| 4,146,581 A | 3/1979 | Nissen et al. |
| 2002/0013501 A1 | 1/2002 | Sorger et al. |

FOREIGN PATENT DOCUMENTS

| JP | 2001-072644 A | 3/2001 | |
| WO | WO 99/12919 | 3/1999 | |
| WO | WO 9912919 | * 3/1999 | |

OTHER PUBLICATIONS

Fors et al., "A Convergent, Scalable Synthesis of HIV Protease Inhibitor PNU–140690," *J.Org. Chem.*, 63(21), 7348–7356 (1998).

Rathke, "The Reformatsky Reaction," *Organic Reactions*, 22, Chapter 4, pp. 424–425, 428–431, John Wiley & Sons, Inc., New York (1975).

Moriwake, "The Reformatsky Reaction. I. Condensation of Ketones and t–Butyl Bromoacetate by Magnesium," *J. Org. Chem.*, 31, 983–985 (1966).

Rosen et al., "Synthesis of Spin Traps Specific for Hydroxyl Radical," *Journal of Medicinal Chemistry*, 31(2), 428–432 (1988).

Sibille et al., "Electrosynthesis of Alcohols from Organic Halides and Ketones or Aldehydes," *Tetrahedron Letters*, 27 (27), 3129–3132 (1986).

Koza, "Organic Synthesis IV—Heteroelement typical metallic element compound," *Courses in Experimental Chemistry*, 4$^{th}$ed., 24, 39–40 (1992).

* cited by examiner

Primary Examiner—Paul J. Killos
Assistant Examiner—Hector M Reyes
(74) Attorney, Agent, or Firm—Leydig, Voit & Mayer, Ltd.

(57) ABSTRACT

The present invention relates to a production method of (R)-3-hydroxy-3-(2-phenylethyl)hexanoic acid which comprises optical resolution of racemic 3-hydroxy-3-(2-phenylethyl)hexanoic acid with an optically active amine of the formula (VIII)

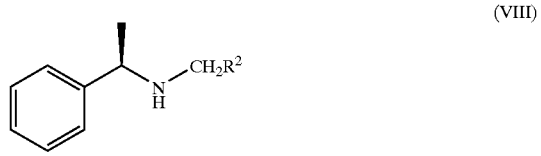

(VIII)

wherein $R^2$ is 3,4-dimethoxyphenyl or 2-chlorophenyl. According to the present invention, (R)-3-hydroxy-3-(2-phenylethyl)hexanoic acid useful as a starting material of a pharmaceutical agent can be efficiently produced with a high optical purity and a relatively high total yield.

18 Claims, No Drawings

PRODUCTION METHOD OF (R)-3 HYDROXY-3-(2-PHENYLETHYL) HEXANOIC ACID AND INTERMEDIATE THEREOF

TECHNICAL FIELD OF THE INVENTION

The present invention relates to a production method of (R)-3-hydroxy-3-(2-phenylethyl)hexanoic acid, which is a useful synthetic intermediate of an anti-HIV agent, and an intermediate thereof.

BACKGROUND OF THE INVENTION

PNU-140690 represented by the following formula (I)

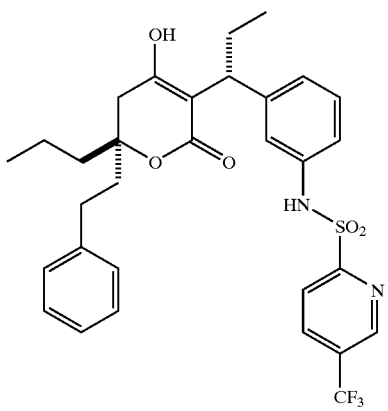

(I)

is known to be useful as an anti-HIV agent being developed in recent years. As a useful synthetic intermediate for PNU-140690, 3-hydroxy-3-(2-phenylethyl)hexanoic acid represented by the following formula (II)

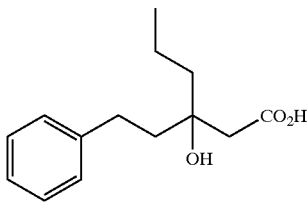

(II)

is known. This 3-hydroxy-3-(2-phenylethyl)hexanoic acid has one asymmetric carbon atom and includes an (R) isomer and an (S) isomer, and only a racemate (racemic 3-hydroxy-3-(2-phenylethyl)hexanoic acid) is synthesized according to a conventional method. Of these, an (R) isomer of the following formula (III)

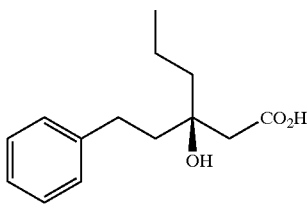

(III)

[(R)-3-hydroxy-3-(2-phenylethyl)hexanoic acid] is preferably used as the above-mentioned synthetic intermediate.

As a method of optical resolution of (R)-3-hydroxy-3-(2-phenylethyl)hexanoic acid from the above-mentioned racemic 3-hydroxy-3-(2-phenylethyl)hexanoic acid, a method using (−)-norephedrine [(1S,2S)-norephedrine] has been conventionally reported (J. Org. Chem., Vol. 63, No. 21, 1998, 7348–7356). According to this method, however, (R)-3-hydroxy-3-(2-phenylethyl)hexanoic acid having an optical purity of not less than 98% e.e. is obtained after two times of recrystallization of a salt with (−)-norephedrine (92% e.e.), which is industrially inefficient. In addition, a method such as this has a problem that the yield of a highly optically pure (R)-3-hydroxy-3-(2-phenylethyl)hexanoic acid throughout the reaction system, in other words, the total yield of highly optically pure (R)-3-hydroxy-3-(2-phenylethyl)hexanoic acid relative to racemic 3-hydroxy-3-(2-phenylethyl)hexanoic acid (hereinafter sometimes to be simply referred to as "total yield") is low (about 27%). In the above-mentioned report, it is described that even the use of generally used amine, such as phenylglycinol, ephedrine, sparteine and α-methylbenzylamine, did not lead to an effective optical resolution, and there is a demand on a method capable of efficiently affording highly optically pure (R)-3-hydroxy-3-(2-phenylethyl)hexanoic acid in a higher total yield.

In the meantime, as an intermediate for the above-mentioned 3-hydroxy-3-(2-phenylethyl)hexanoic acid, racemic ethyl 3-hydroxy-3-(2-phenylethyl)hexanoate of the following formula (IV)

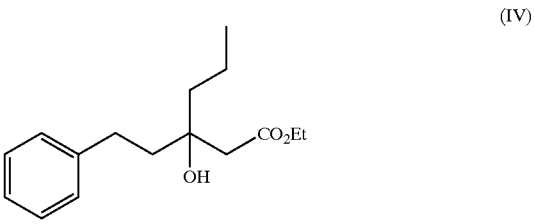

(IV)

is known.

As a method for producing such racemic ethyl 3-hydroxy-3-(2-phenylethyl)hexanoate, a method comprising addition of a lithium salt of ethyl acetate to 1-phenyl-3-hexanone in tetrahydrofuran (THF) is known. For preparation of a lithium salt of ethyl acetate, however, deprotonation from ethyl acetate with a strong base such as lithium dialkylamide and the like is necessary, which is generally conducted by a reaction at an ultra-low temperature at around −78° C. (WO99/12919, Kristina S Fors et al, J. Org. Chem. 1998, 63, 7348–7356). A reaction at such an ultra-low temperature contains many industrially disadvantageous aspects, for example, it requires a special cooling unit and the operation is complicated and the like.

As a method for producing racemic ethyl 3-hydroxy-3-(2-phenylethyl)hexanoate in a temperature range that does not require a special cooling unit, the use of Reformatskii reaction is considered. The Reformatskii reaction is a conventionally known reaction which produces β-hydroxyacid ester by condensation of α-halogen ester and a carbonyl compound such as aldehyde, ketone and the like in the presence of zinc. For this Reformatskii reaction to proceed smoothly, the above-mentioned zinc needs to have a high activity (reactivity). As a method for producing activated zinc, the following conventional methods (1)–(5) are known. Any activated zinc obtained by these methods has a problem as shown in the following. The method is not practical for use for the above-mentioned Reformatskii reaction and racemic ethyl 3-hydroxy-3-(2-phenylethyl)hexanoate could not be obtained in a sufficient yield.

(1) A Method for Preparing Metallic Zinc by Reducing Zinc Salt Such as Zinc Chloride and the Like with Potassium, Magnesium, Lithium and the Like.

This method has a problem in safety because a water-prohibiting metal is used and the like.

(2) A Method for Activating Metallic Zinc with Hydrochloric Acid.

According to this method, application to a Reformatskii reaction, which is a water-prohibiting reaction, requires activation of zinc, complete removal of the acid and drying, and the preparation is complicated and impractical.

(3) A Method for Activating Zinc by treating Metallic Zinc with a Copper Salt or Silver Salt in Acetic Acid to Give an Alloy with Copper or Silver.

Because alloy is prepared in acetic acid, acetic acid needs to be completely removed by washing with water, and only after drying on washing with water, can it be used for a Reformatskii reaction, which is a water-prohibiting reaction, and the preparation is complicated and impractical.

(4) A Method for Activating Zinc by Ultrasonic Wave.

In this method, every facility used for the production of activated zinc requires a sufficiently strong ultrasonic oscillator. Therefore, this method is not entirely practical.

(5) A Method for Activating Zinc by Stirring Zinc with Chlorotrimethylsilane in Ether.

This method is defective in that a highly inflammable solvent such as ether is used and the activity of the obtained zinc is not always high enough.

In the reaction using the above-mentioned activated zinc, a waste containing zinc is produced and a special waste treatment is necessary to avoid environmental pollution.

In the above-mentioned reaction, a bromoacetic acid ester is used. Bromoacetic acid ester is expensive and shows strong tearing property, and the reaction using the same has safety and health problems.

The present invention has been made to solve the above-mentioned problems and aims at providing a production method capable of efficient production of (R)-3-hydroxy-3-(2-phenylethyl)hexanoic acid useful as a starting material of a pharmaceutical agent from racemic 3-hydroxy-3-(2-phenylethyl)hexanoic acid, with a high optical purity and in a relatively high total yield.

In addition, another object of the present invention is to provide a method of producing 3-hydroxy-3-(2-phenylethyl)hexanoic acid ester safely and at a lower cost than a conventional method, by the use of general production apparatuses.

As a result of intensive studies in an attempt to solve the above-mentioned problems, the present inventors have completed the present invention. The present invention provides the following.

DISCLOSURE OF THE INVENTION

[1] A production method of (R)-3-hydroxy-3-(2-phenylethyl)hexanoic acid, which comprises optically resolving racemic 3-hydroxy-3-(2-phenylethyl)hexanoic acid using an optically active amine of the formula (VIII)

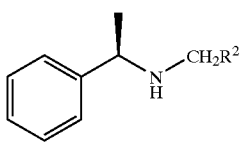

(VIII)

wherein $R^2$ is 3,4-dimethoxyphenyl or 2-chlorophenyl (hereinafter to be also referred to as "optically active amine (VIII)").

[2] The production method of the above-mentioned [1], wherein a salt of (R)-3-hydroxy-3-(2-phenylethyl)hexanoic acid with the optically active amine (VIII) is crystallized in one or more kinds of solvents selected from ethyl acetate, methanol, isopropanol, ethanol, acetonitrile, methyl isobutyl ketone (MIBK), acetone, methyl ethyl ketone, diisopropyl ether, dimethoxyethane and THF, wherein the solvent optionally further contains water.

[3] The production method of the above-mentioned [1], wherein the optically active amine (VIII) is obtained by condensing (R)-1-phenylethylamine with a compound of the formula $R^2$—CHO (VIII-i) wherein $R^2$ is as defined above, and reducing the resulting compound.

[4] The production method of the above-mentioned [1], which comprises recovering the optically active amine (VIII) after optical resolution.

[5] A production method of (R)-3-hydroxy-3-(2-phenylethyl)hexanoic acid, which comprises hydrolyzing a racemic 3-hydroxy-3-(2-phenylethyl)hexanoic acid ester to produce racemic 3-hydroxy-3-(2-phenylethyl)hexanoic acid, extracting the compound with one or more kinds of solvents selected from ethyl acetate, MIBK, methyl ethyl ketone, diisopropyl ether and THF, and optically resolving the compound by crystallizing a salt of (R)-3-hydroxy-3-(2-phenylethyl)hexanoic acid with an optically active amine (VIII) using a part or the entirety left of the extraction solvent as a solvent for optical resolution.

[6] The production method of the above-mentioned [5], wherein the optically active amine (VIII) is produced by condensing (R)-1-phenylethylamine with a compound of the formula $R^2$—CHO (VIII-i) wherein $R^2$ is as defined above, and reducing the resulting compound.

[7] The production method of the above-mentioned [5], which comprises recovering the optically active amine (VIII) after optical resolution.

[8] A production method of (R)-3-hydroxy-3-(2-phenylethyl)hexanoic acid, which comprises reacting magnesium, a haloacetic acid ester and 1-phenyl-3-hexanone to produce racemic 3-hydroxy-3-(2-phenylethyl)hexanoic acid ester, hydrolyzing this compound to give racemic 3-hydroxy-3-(2-phenylethyl)hexanoic acid, and optically resolving this compound using the optically active amine (VIII).

[9] The production method of the above-mentioned [8], wherein the haloacetic acid ester is a chloroacetic acid ester.

[10] The production method of the above-mentioned [8], wherein a salt of the (R)-3-hydroxy-3-(2-phenylethyl)hexanoic acid with the optically active amine (VIII) is crystallized in one or more kinds of solvents selected from ethyl acetate, methanol, isopropanol, ethanol, acetonitrile, MIBK, acetone, methyl ethyl ketone, diisopropyl ether, dimethoxyethane and THF, wherein the solvent optionally further contains water.

[11] The production method of the above-mentioned [8], wherein, after producing the racemic 3-hydroxy-3-(2-phenylethyl)hexanoic acid, the resulting compound is extracted with one or more kinds of solvents selected from ethyl acetate, MIBK, methyl ethyl ketone, diisopropyl ether and THF, and optically resolved by crystallizing the salt of (R)-3-hydroxy-3-(2-phenylethyl)hexanoic acid with an optically active amine (VIII) using a part or the entirety left of the extraction solvent as a solvent for optical resolution.

[12] The production method of the above-mentioned [8], wherein the optically active amine (VIII) is obtained by condensing (R)-1-phenylethylamine with a compound of the formula $R^2$—CHO (VIII-i) wherein $R^2$ is as defined above, and reducing the resulting compound.

[13] The production method of the above-mentioned [8], which comprises recovering the optically active amine (VIII) after optical resolution.

[14] The production method of the above-mentioned [8], wherein magnesium is activated.

[15] The production method of the above-mentioned [14], wherein magnesium is activated with chlorosilanes and halogenated hydrocarbon.

[16] The production method of the above-mentioned [15], wherein the chlorosilanes is selected from the group consisting of chlorotrimethylsilane, dichlorodimethylsilane, methyltrichlorosilane and tetrachlorosilane.

[17] The production method of the above-mentioned [15], wherein the halogenated hydrocarbon is selected from the group consisting of allyl bromide, iodomethane, iodoethane, benzyl bromide, 1,2-diiodoethane and 1,2-dibromoethane.

[18] The production method of the above-mentioned [8], wherein 1-phenyl-3-hexanone is obtained by condensing benzaldehyde with 2-pentanone in the presence of a base to give propyl styryl ketone, and reducing the obtained propyl styryl ketone.

[19] A production method of a racemic 3-hydroxy-3-(2-phenylethyl)hexanoic acid ester, which comprises reacting magnesium, haloacetic acid ester and 1-phenyl-3-hexanone.

[20] The production method of the above-mentioned [19], wherein the haloacetic acid ester is a chloroacetic acid ester.

[21] The production method of the above-mentioned [19], wherein magnesium is activated.

[22] The production method of the above-mentioned [21], wherein magnesium is activated with chlorosilanes and halogenated hydrocarbon.

[23] The production method of the above-mentioned [22], wherein chlorosilanes is selected from the group consisting of chlorotrimethylsilane, dichlorodimethylsilane, methyltrichlorosilane and tetrachlorosilane.

[24] The production method of the above-mentioned [22], wherein halogenated hydrocarbon is selected from the group consisting of allyl bromide, iodomethane, iodoethane, benzyl bromide, 1,2-diiodoethane and 1,2-dibromoethane.

[25] The production method of the above-mentioned [19], wherein 1-phenyl-3-hexanone is obtained by condensing benzaldehyde with 2-pentanone in the presence of a base to give propyl styryl ketone, and reducing the obtained propyl styryl ketone.

DETAILED DESCRIPTION OF THE INVENTION

In the present specification, the term "racemic" is used to show that the compound preceded by this term is a mixture of enantiomers ((R)-isomer and (S)-isomer) that can be optically resolved, and is not to be construed as limiting the compound only to a mixture of equivalent amounts of (R)-isomer and (S)-isomer.

The production method of the present invention comprises, as shown in the following reaction scheme 1, a part or the entirety of the steps of (a): a step for producing a racemic 3-hydroxy-3-(2-phenylethyl)hexanoic acid ester of the formula (VII) (hereinafter to be also referred to as "racemic carboxylic acid ester (VII)") by reacting 1-phenyl-3-hexanone of the formula (V) (hereinafter to be also referred to as "ketone (V)"), a haloacetic acid ester of the formula (VI) (hereinafter to be also referred to as "ester (VI)") and magnesium, (b): a step for producing racemic 3-hydroxy-3-(2-phenylethyl)hexanoic acid of the formula (II) (hereinafter to be also referred to as "racemic carboxylic acid (II)") by hydrolyzing the racemic carboxylic acid ester (VII), and (c): a step for producing (R)-3-hydroxy-3-(2-phenylethyl) hexanoic acid of the formula (III) (hereinafter to be also referred to as "(R)-carboxylic acid (III)") by optical resolution of racemic carboxylic acid (II) using the optically active amine (VIII).

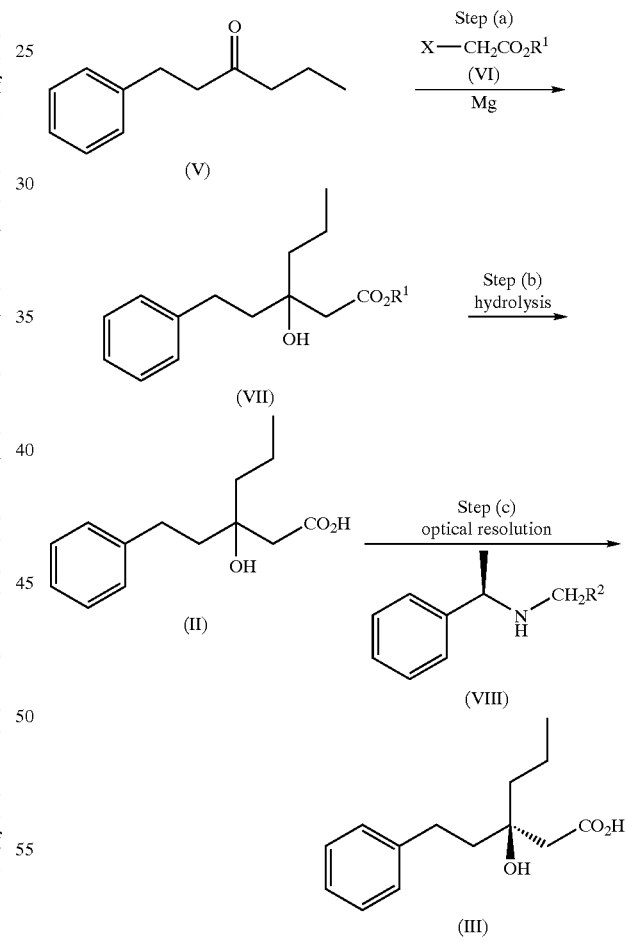

wherein $R^1$ is free of particular limitation as long as it does not influence the reaction, X is a halogen atom and $R^2$ is 3,4-dimethoxyphenyl or 2-chlorophenyl.

Each step is explained in the following.

1. Production Step of Racemic 3-hydroxy-3-(2-phenylethyl) hexanoic Acid Ester [Step (a)]

This step (a) comprises, as shown in the above-mentioned scheme 1, reacting 1-phenyl-3-hexanone [ketone (V)], haloacetic acid ester [ester (VI)] and magnesium to give racemic 3-hydroxy-3-(2-phenylethyl)hexanoic acid ester [racemic carboxylic acid ester (VII)].

This reaction is realized by, for example, simultaneously adding ketone (V) and ester (VI) to magnesium charged in the solvent in advance, or adding ester (VI) to a mixture of ketone (V) and magnesium charged in the solvent in advance.

In the above-mentioned reaction, the amount of magnesium to be used is preferably 1 mole–5 moles, per 1 mole of ketone (V), but from an economic aspect, it is more preferably 1.1 moles-2.0 moles. In the above-mentioned reaction, when the amount of magnesium to be used is less than 1 mole per 1 mole of ketone (V), ketone (V) partly may remain unreacted, thereby possibly lowering the reaction efficiency. In the above-mentioned reaction, moreover, the use of magnesium in a proportion of more than 5 moles per 1 mole of ketone (V) is economically useless, because the amount of magnesium unrelated to the reaction becomes large.

In the above-mentioned reaction, the amount of ester (VI) to be used is preferably 1 mole–3 moles per 1 mole of ketone (V), but from the economic aspect, it is more preferably 1 mole–2 moles. In the above-mentioned reaction, when the amount of ester (VI) to be used is less than 1 mole per 1 mole of ketone (V), ketone (V) partly may remain unreacted, thereby possibly lowering the reaction efficiency. In the above-mentioned reaction, moreover, when the amount of ester (VI) to be used exceeds 3 moles per 1 mole of ketone (V), it is economically useless, because the amount of ester (VI) unrelated to the reaction becomes large, and moreover, the ester remained in the resulting product may make purification of the product difficult.

The ester (VI) to be used for the above-mentioned step (a) is free of any particular limitation as long as X is a halogen atom and $R^1$ does not influence the reaction. X in the formula (VI) is exemplified by chlorine atom, bromine atom, iodine atom and the like, with preference given to chlorine atom. As $R^1$ in the formula (VI), straight or branched chain alkyl group having 1–6 carbon atoms (e.g., methyl, ethyl, isopropyl, n-butyl, isobutyl, sec-butyl, tert-butyl, pentyl, isopentyl, neopentyl, hexyl, etc.) is exemplified, with preference given to straight or branched chain alkyl group having 1–4 carbon atoms (e.g., methyl, ethyl, isopropyl, n-butyl, isobutyl, sec-butyl, tert-butyl, etc.).

As preferable ester (VI), a chloroacetic acid ester, wherein X of the formula (VI) is chlorine atom, is mentioned, more preferably a chloroacetic acid alkyl ester, wherein X is chlorine atom and $R^1$ is straight or branched chain alkyl group having 1–6, preferably 1–4, carbon atoms. Specific examples thereof include methyl chloroacetate, ethyl chloroacetate, isopropyl chloroacetate, n-butyl chloroacetate, tert-butyl chloroacetate and the like. Of these, use of ethyl chloroacetate or tert-butyl chloroacetate is preferable, because it is easily obtained.

The above-mentioned reaction is generally carried out in a temperature range of 15° C.–100° C., preferably 20° C.–70° C. When the reaction temperature is lower than 15° C., the reaction may proceed slowly or may not proceed at all. When the reaction temperature exceeds 100° C., the starting material, ketone (V), may be decomposed in the reaction mixture, or the resulting product, racemic carboxylic acid ester (VII) may be decomposed, thus lowering the yield of the reaction.

The above-mentioned reaction is generally carried out in 30 min–20 hr by the addition of ester (VI) to a mixture of ketone (V) and magnesium, or by the simultaneous addition of ketone (V) and ester (VI) to magnesium.

The solvent to be used for the above-mentioned reaction may be any as long as it does not inhibit the reaction, and ethers such as THF, dioxane, dimethoxyethane and the like and a mixed solvent of the ethers and any solvent selected from aromatic hydrocarbons such as benzene, toluene, xylene and the like, aliphatic hydrocarbons such as heptane, hexane, octane and the like can be preferably used. When a mixed solvent is to be used, a typical conventionally-known mixing ratio may be applied for mixing.

The amount of the solvent to be used is generally 100 mL–2000 mL, preferably 150 mL–1500 mL, per 1 mole of ketone (V) for smooth reaction and improved productivity by reaction.

By the above-mentioned step (a), racemic carboxylic acid ester (VII) can be produced safely at a lower cost than by a conventional manner.

That is, because the above-mentioned step (a) differs from a conventional method that uses lithium dialkylamide, and does not require a reaction at around an ultra-low temperature (around −78° C.), production can be done efficiently without a need for a special cooling unit. In addition, because expensive lithium dialkylamide is not used, racemic carboxylic acid ester (VII) can be produced at a lower cost. According to the above-mentioned step (a), moreover, a highly inflammable solvent is not used, unlike methods using activated zinc and ethyl bromoacetate, and therefore, the method is safe and can conveniently produce racemic carboxylic acid ester (VII) without a waste treatment. The activation of magnesium is easy as compared to the aforementioned preparation of activated zinc, and the operation of the production is efficient. In the above-mentioned step (a), moreover, haloacetic acid ester (e.g., chloroacetic acid ester) other than expensive and highly tearing bromoacetic acid ester can be used, in which case racemic carboxylic acid ester (VII) can be produced at a low cost without any safety or hygienic problem.

In the above-mentioned step (a), magnesium to be used is preferably activated. In the above-mentioned step (a), magnesium, whether activated or not, affords the above-mentioned effect, but the use of activated magnesium makes the reaction to produce racemic carboxylic acid ester (VII) smooth and safer.

As used herein, by the "activation of magnesium" is meant removal of a substance inhibiting reaction on magnesium surface (in many cases it is a film of magnesium oxide) to enhance the reactivity. As a method for activating magnesium, for example, (1) activation by a combination of chlorotrimethylsilane and zinc chloride, (2) activation by chlorotrimethylsilane alone, (3) activation by iodine alone, (4) activation by a combination of iodine and ethyl bromoacetate, (5) activation by a combination of chlorosilanes and halogenated hydrocarbon, and the like are mentioned (hereinafter "chlorotrimethylsilane and zinc chloride" to be used for the method of the above-mentioned (1), "chlorotrimethylsilane" to be used for the method of the above-mentioned (2), "iodine" to be used for the method of the above-mentioned (3), "iodine and ethyl bromoacetate" to be used for the method of the above-mentioned (4) and "chlorosilanes and halogenated hydrocarbon" to be used for the method of the above-mentioned (5) are also collectively referred to as "activator"). Of these, the activation method by chlorotrimethylsilane alone of the above-mentioned (2) is more preferable, because activation is easy and a starting material difficult to handle is not used. In addition, the activation method by chlorosilanes and halogenated hydrocarbon of the above-mentioned (5) is more preferable, because magnesium can be more effectively activated than iodine, iodomethane, chlorotrimethylsilane and the like used alone.

For the activation of magnesium in the above-mentioned step (a), an activator only needs to be added immediately before or simultaneously with the start of the reaction of magnesium, ketone (V) and ester (VI) in a solvent in the above-mentioned reaction.

To be specific, an activator is added to magnesium charged in the solvent in advance, or a mixture of ketone (V), ester (VI) and an activator is added, or a mixture of ketone (V) and ester (VI) and an activator may be added separately, to magnesium charged in the solvent in advance. Alternatively, a mixture of ester (VI) and an activator is added, or ester (VI) and an activator may be added separately, to a mixture of ketone (V) and magnesium charged in the solvent in advance. When the above-mentioned activator is separately added, it is preferably added immediately before addition of a mixture of ketone (V) and ester (VI) or ester (VI), or simultaneously added (more preferably simultaneously added in a thin stream). For addition of the above-mentioned activator, a part of ketone (V) and ester (VI) is added in advance and an activator is added and stirred for a suitable period of time (or stirring and suitable temperature rise), after which the remaining ketone (V) and ester (VI) may be added. When the activator is to be added separately, the activator may be prepared into a solution containing the activator in advance depending on the kind thereof. In this case, the solvent therefor is preferably the aforementioned solvent used for the reaction.

Each method for activating magnesium in the above-mentioned step (a) is specifically explained in the following.

(1) Activation by Chlorotrimethylsilane and Zinc Chloride in Combination

When magnesium is activated by combining chlorotrimethylsilane and zinc chloride, the amount of chlorotrimethylsilane to be used is preferably 0.005 mole–0.05 mole, more preferably 0.01 mole–0.05 mole, per 1 mole of magnesium. When the amount of chlorotrimethylsilane to be used is less than 0.005 mole per 1 mole of magnesium, magnesium may not be sufficiently activated and the objective reaction may not be started smoothly. When the amount of chlorotrimethylsilane to be used exceeds 0.05 mole per 1 mole of magnesium, magnesium may be consumed by the reaction with chlorotrimethylsilane, thereby possibly necessitating an excess amount of magnesium to complete the reaction, which is economically disadvantageous.

The amount of zinc chloride to be used is preferably 0.01 mole–0.1 mole, more preferably 0.01 mole–0.07 mole, per 1 mole of magnesium. When the amount of zinc chloride to be used is less than 0.01 mole per 1 mole of magnesium, magnesium may not be sufficiently activated and the objective reaction may not be started smoothly. When the amount of zinc chloride to be used exceeds 0.1 mole per 1 mole of magnesium, magnesium may be consumed by the reaction with zinc chloride, thereby possibly necessitating an excess amount of magnesium to complete the reaction, which is economically disadvantageous.

In a method for producing racemic carboxylic acid ester (VII) in the above-mentioned step (a), when magnesium is activated by combining chlorotrimethylsilane and zinc chloride, the temperature of the above-mentioned reaction conditions is particularly preferably in the range of 25° C.–70° C. from the aforementioned range, and the time is particularly preferably 2 hr–10 hr from the aforementioned range.

When magnesium is activated by combining chlorotrimethylsilane and zinc chloride as mentioned above, activation is performed particularly effectively as compared to activation of magnesium by a different method. This is beneficial because the objective reaction can be started at a lower temperature.

(2) Activation by Chlorotrimethylsilane Alone

In the above-mentioned step (a), magnesium may be activated using chlorotrimethylsilane alone. The amount of chlorotrimethylsilane to be used is preferably 0.005 mole–0.2 mole, more preferably 0.01 mole–0.1 mole, per 1 mole of magnesium. When the amount of chlorotrimethylsilane to be used is less than 0.005 mole per 1 mole of magnesium, magnesium may not be sufficiently activated and the objective reaction may not be started smoothly. When the amount of chlorotrimethylsilane to be used exceeds 0.1 mole per 1 mole of magnesium, magnesium may be consumed by the reaction with chlorotrimethylsilane, thereby possibly necessitating an excess amount of magnesium to complete the reaction, which is economically disadvantageous.

In a method for producing racemic carboxylic acid ester (VII) in the above-mentioned step (a), when magnesium is activated by chlorotrimethylsilane alone, the temperature of the above-mentioned reaction conditions is particularly preferably in the range of 20° C.–60° C. from the aforementioned range, and the time is particularly preferably 2 hr–10 hr from the aforementioned range.

When magnesium is activated by using chlorotrimethylsilane alone as mentioned above, activation of magnesium is performed particularly effectively as compared to activation of magnesium by a different method. This is beneficial because the objective reaction can be started at a lower temperature and elements problematic to the environment do not need to be used.

(3) Activation by Iodine Alone

In the above-mentioned step (a), magnesium may be activated using iodine alone as an activator. The amount of iodine to be used is preferably 0.0001 mole–0.01 mole and more preferably 0.0003 mole–0.002 mole, per 1 mole of magnesium. When the amount of iodine to be used is less than 0.0001 mole per 1 mole of magnesium, magnesium may not be sufficiently activated and the objective reaction may not be started smoothly. When the amount of iodine to be used exceeds 0.01 mole per 1 mole of magnesium, magnesium may be consumed by the reaction with iodine, thereby possibly necessitating an excess amount of magnesium to complete the reaction, which is economically disadvantageous.

In a method for producing racemic carboxylic acid ester (VII) in the above-mentioned step (a), when magnesium is activated by iodine alone, the temperature of the above-mentioned reaction conditions is particularly preferably in the range of 25° C.–65° C. from the aforementioned range, and the time is particularly preferably 2 hr–10 hr from the aforementioned range.

By using iodine alone for activation of magnesium as mentioned above, particularly the brown color of the reaction solution disappears when magnesium is activated, when compared to the case where magnesium is activated by other method, which advantageously facilitates confirmation of activation.

(4) Activation by Iodine and Ethyl Bromoacetate in Combination

In the above-mentioned step (a), ethyl bromoacetate may be used in addition to the above-mentioned iodine to activate magnesium. When magnesium is activated by combining iodine and ethyl bromoacetate, the amount of iodine to be used is preferably 0.0001 mole–0.01 mole, more preferably 0.0003 mole–0.002 mole, per 1 mole of magnesium for the same reason as given for the above-mentioned (3).

The amount of ethyl bromoacetate to be used is preferably 0.001 mole–0.01 mole, more preferably 0.002 mole–0.005 mole, per 1 mole of magnesium. When the amount of ethyl bromoacetate to be used is less than 0.001 mole per 1 mole of magnesium, magnesium may not be sufficiently activated and the objective reaction may not be started smoothly. When the amount of ethyl bromoacetate to be used exceeds 0.01 mole per 1 mole of magnesium, magnesium may be consumed by the reaction with ethyl bromoacetate, thereby possibly necessitating an excess amount of magnesium to complete the reaction, which is economically disadvantageous.

In a method for producing racemic carboxylic acid ester (VII) in the above-mentioned step (a), when magnesium is activated by combining iodine and ethyl bromoacetate, the temperature of the above-mentioned reaction conditions is particularly preferably in the range of 35° C.–70° C. from the aforementioned range, and the time is particularly preferably 2 hr–10 hr from the aforementioned range. In this case, iodine may be added first and then ethyl bromoacetate may be added.

By using iodine and ethyl bromoacetate in combination for activation of magnesium as mentioned above, particularly the reaction mixture turn to bear a green color along with the activation of magnesium, when compared to the case where magnesium is activated by other method, which advantageously facilitates confirmation of activation.

(5) Activation by Chlorosilanes and Halogenated Hydrocarbon in Combination

A method for producing racemic 3-hydroxy-3-(2-phenylethyl)hexanoic acid ester by activation of magnesium by a combination of the chlorosilanes and halogenated hydrocarbon is applicable to the production of other 3-hydroxycarboxylic acid esters. This method is explained in the following including the production of other 3-hydroxycarboxylic acid esters.

This method is, as shown in the following scheme, a production method comprising reacting a carbonyl compound of the formula (i) (hereinafter to be also referred to as "carbonyl compound (i)"), the above-mentioned ester (VI) and magnesium activated by chlorosilanes and halogenated hydrocarbon to give 3-hydroxycarboxylic acid ester (ii) of the formula (ii) (hereinafter to be also referred to as "ester (ii)"), such as the above-mentioned racemic 3-hydroxy-3-(2-phenylethyl)hexanoic acid ester [racemic carboxylic acid ester (VII)].

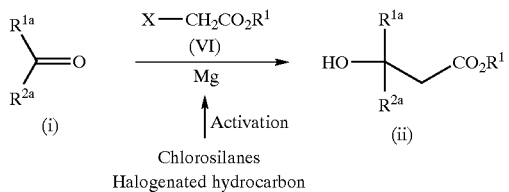

wherein $R^{1a}$ and $R^{2a}$ are free of particular limitation as long as they do not show an influence on the reaction, and $R^1$ and X are as defined above.

The carbonyl compound (i) to be used for this production method is not subject to any particular limitation as long as it is aldehyde or ketone that can react with ester (VI) to give ester (ii). For example, aldehyde or ketone of the formula (i), wherein $R^{1a}$ is a lower alkyl group optionally having substituents, an aryl group optionally having substituents, an aralkyl group optionally having substituents and the like, and $R^{2a}$ is hydrogen atom, a lower alkyl group optionally having substituents, an aryl group optionally having substituents, an aralkyl group optionally having substituents can be mentioned. Specific examples include acetaldehyde, benzaldehyde, acetone, methyl ethyl ketone, acetophenone, benzophenone, 1-phenyl-3-hexanone [the above-mentioned ketone (V)] and the like, with preference given to 1-phenyl-3-hexanone [the above-mentioned ketone (V)] because it is a synthetic intermediate for PNU-140690 useful as an anti-HIV agent.

As the "lower alkyl group" of the "lower alkyl group optionally having substituents" for the above-mentioned $R^{1a}$ and $R^{2a}$, a straight or branched chain alkyl group having 1–10, preferably 2–7, carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl and the like, with preference given to propyl, isopropyl, butyl, pentyl, hexyl, heptyl and the like.

The "aryl group" of the "aryl group optionally having substituents" for the above-mentioned $R^{1a}$ and $R^{2a}$ is exemplified by phenyl, 1-naphthyl, 2-naphthyl, 1-anthryl, 2-anthryl, 9-anthryl and the like, with preference given to phenyl, 1-naphthyl, 2-naphthyl and the like.

The "aralkyl group" of the "aralkyl group optionally having substituents" for the above-mentioned $R^{1a}$ and $R^{2a}$ is exemplified by an aralkyl group wherein the aryl moiety is the same as the above-mentioned "aryl group" and the alkyl moiety has 1–10, preferably 2–5, carbon atoms. Examples thereof include benzyl, 1-phenethyl, 2-phenethyl, 3-phenylpropyl and the like, with preference given to 2-phenethyl and the like.

The "substituent" of the "lower alkyl group optionally having substituents", "aryl group optionally having substituents" and "aralkyl group optionally having substituents" for the above-mentioned $R^{1a}$ and $R^{2a}$ is not subject to any particular limitation as long as it does not inhibit the reaction, and is exemplified by lower alkyl group (such as those mentioned above, that cannot be a substituent for the "lower alkyl group optionally having substituents"), halogen atom (e.g., fluorine atom, chlorine atom, bromine atom, iodine atom, etc.), lower alkoxy group, aryloxy group, aralkyloxy group, dialkylamino group and the like. The number of the substituent is not particularly limited and is preferably 1–3, wherein the substituents may be the same or different.

As the "lower alkoxy group" for the above-mentioned substituent, a linear or branched chain alkoxy group having carbon atoms 1–10 can be mentioned, which is exemplified by methoxy, ethoxy, propoxy, isopropoxy, butoxy, isobutoxy, sec-butoxy, tert-butoxy, pentyloxy, isopentyloxy, neopentyloxy, hexyloxy and the like.

As the "aryloxy group" for the above-mentioned substituent, phenoxy, 1-naphthoxy, 2-naphthoxy, 1-anthryloxy, 2-anthryloxy, 9-anthryloxy and the like can be mentioned.

As the "aralkyloxy group" for the above-mentioned substituent, benzyloxy, 1-phenethyloxy, 2-phenethyloxy, 3-phenylpropoxy and the like can be mentioned.

As the "dialkylamino group" for the above-mentioned substituent, a dialkylamino group having linear or branched chain alkyl moiety having 1–6 carbon atoms can be mentioned, wherein the alkyl moieties are the same or different. Examples thereof include dimethylamino, diethylamino, ethylmethylamino and the like.

The "chlorosilanes" to be used for the above-mentioned method are not subject to any particular limitation as long as they can activate magnesium. Examples thereof include chlorosilanes of the formula (iii)

$$R^{3a}{}_n SiCl_{(4-n)} \qquad\qquad (iii)$$

wherein $R^{3a}$ is a lower alkyl group or aryl group and n is an integer of 0–3. As the "lower alkyl group" and "aryl group"

for $R^{3a}$, those exemplified for the "lower alkyl groups" and "aryl group" of the above-mentioned $R^{1a}$ and $R^{2a}$ can be mentioned.

Chlorosilanes are concretely exemplified by chlorotrimethylsilane, dichlorodimethylsilane, methyltrichlorosilane, tetrachlorosilane and the like.

The "halogenated hydrocarbon" to be used for the above-mentioned method is not subject to any particular limitation as long as it can activate magnesium. Examples thereof include hydrocarbon wherein 1 or 2 optional hydrogen atoms are substituted by halogen atom. By the "halogen atom" is meant chlorine atom, bromine atom, iodine atom and the like, and by the "hydrocarbon" is meant straight or branched chain alkane, alkene, alkyne and the like, having 1–10, preferably 1–7, carbon atoms and optionally having substituents. Examples of the substituent include aryl group (e.g., phenyl group, 1-naphthyl, 2-naphthyl, etc.) and the like.

As the halogenated hydrocarbon, allyl bromide, iodomethane, iodoethane, benzyl bromide, 1,2-diiodoethane, 1,2-dibromoethane and the like are specifically mentioned, with preference given to allyl bromide, iodomethane and 1,2-dibromoethane.

The above-mentioned method is realized by simultaneous addition of carbonyl compound (i) and ester (VI) to magnesium charged in a solvent in advance, or by the addition of ester (VI) to a mixture of carbonyl compound (i) and magnesium charged in a solvent in advance.

In the above-mentioned method, chlorosilanes and halogenated hydrocarbon are added to activate magnesium. As used herein, by the "activate magnesium" is meant removing a substance on magnesium surface that inhibits reaction (in many cases, it is a film of oxidized magnesium) to enhance reactivity.

The activation of magnesium by chlorosilanes and halogenated hydrocarbon may be conducted immediately before the start of the reaction or along with the progress of the reaction or both. To be specific, chlorosilanes and halogenated hydrocarbon are added to magnesium charged in a solvent in advance; a mixture of carbonyl compound (i), ester (VI), chlorosilanes and halogenated hydrocarbon is added to magnesium charged in a solvent in advance; a mixture of carbonyl compound (i) and ester (VI), and a mixture of chlorosilanes and halogenated hydrocarbon are separately added to magnesium charged in a solvent in advance; halogenated hydrocarbon is added to magnesium charged in a solvent in advance, and then a mixture of carbonyl compound (i), ester (VI) and chlorosilanes is added; halogenated hydrocarbon is added to magnesium charged in a solvent in advance, and then a mixture of carbonyl compound (i) and ester (VI), and chlorosilanes are separately added; halogenated hydrocarbon is added to magnesium charged in a solvent in advance, and then a mixture of carbonyl compound (i), ester (VI), chlorosilanes and halogenated hydrocarbon is added; halogenated hydrocarbon is added to magnesium charged in a solvent in advance, and then a mixture of carbonyl compound (i) and ester (VI), and a mixture of chlorosilanes and halogenated hydrocarbon are separately added; a mixture of ester (VI), chlorosilanes and halogenated hydrocarbon is added to a mixture of carbonyl compound (i) and magnesium charged in a solvent in advance; ester (VI), and a mixture of chlorosilanes and halogenated hydrocarbon is separately added to a mixture of carbonyl compound (i) and magnesium charged in a solvent in advance; halogenated hydrocarbon is added to a mixture of carbonyl compound (i) and magnesium charged in a solvent in advance, and then a mixture of ester (VI), chlorosilanes and halogenated hydrocarbon is added; halogenated hydrocarbon is added to a mixture of carbonyl compound (i) and magnesium charged in a solvent in advance, and then ester (VI) and a mixture of chlorosilanes and halogenated hydrocarbon is added separately and the like, but the activation is not limited to these. When chlorosilanes or halogenated hydrocarbon is added separately, they are preferably added immediately before addition of a mixture of carbonyl compound (i) and ester (VI) or ester (VI), or simultaneously therewith (more preferably simultaneously added in a thin stream). For the addition of the above-mentioned chlorosilanes or halogenated hydrocarbon, a part of carbonyl compound (i) and ester (VI) are added, chlorosilane or halogenated hydrocarbon is added and stirred for a suitable time (or stirring and suitable temperature rise), and then the remaining carbonyl compound (i) and ester (VI) may be added. When chlorosilane or halogenated hydrocarbon is added separately, it may be prepared in advance into a solvent containing the same.

In the above-mentioned reaction, the amount of magnesium to be used is preferably 0.5 mole–5 moles per 1 mole of carbonyl compound (i), but it is more preferably 0.9 mole–2 moles from the economic aspect. In the above-mentioned reaction, when the amount of magnesium to be used is less than 0.5 mole per 1 mole of carbonyl compound (i), the efficiency of the reaction may be unpreferably degraded markedly due to the carbonyl compound (i) remaining partially unreacted. In the above-mentioned reaction, moreover, the use of magnesium in excess of 5 moles per 1 mole of carbonyl compound (i) is economically useless, because it leads to the use of a large amount of magnesium not involved in the reaction.

In the above-mentioned reaction, the amount of ester (VI) to be used is preferably 1 mole–3 moles per 1 mole of carbonyl compound (i), more preferably 1 mole–2 moles from the economic aspect. In the above-mentioned reaction, when the amount of ester (VI) to be used is less than 1 mole per 1 mole of carbonyl compound (i), the efficiency of the reaction may be markedly degraded due to the carbonyl compound (i) remaining partially unreacted. In the above-mentioned reaction, moreover, the use of ester (VI) in excess of 3 moles per 1 mole of carbonyl compound (i) is economically useless and makes purification of the product difficult as well, because it leads to the use of a large amount of ester unnecessary for the reaction with carbonyl compound (i).

In the above-mentioned reaction, the amount of chlorosilanes to be used is preferably 0.005 mole–0.2 mole, more preferably 0.01 mole–0.05 mole, per 1 mole of magnesium. When the amount of chlorosilanes to be used is less than 0.005 mole per 1 mole of magnesium, magnesium may not be sufficiently activated and the objective reaction may not be started smoothly. When the amount of chlorosilanes to be used exceeds 0.2 mole per 1 mole of magnesium, magnesium may be consumed by the reaction with chlorosilanes, thereby possibly necessitating an excess amount of magnesium to complete the reaction, which is economically disadvantageous.

In the above-mentioned reaction, the amount of halogenated hydrocarbon to be used is preferably 0.001 mole–0.2 mole, more preferable 0.005 mole–0.05 mole, per 1 mole of magnesium. When the amount of halogenated hydrocarbon to be used is less than 0.001 mole per 1 mole of magnesium, magnesium may not be sufficiently activated and the objective reaction may not be started smoothly. When the amount of halogenated hydrocarbon to be used exceeds 0.2 mole per 1 mole of magnesium, magnesium may be consumed by the reaction with halogenated hydrocarbon, thereby possibly necessitating an excess amount of magnesium to complete the reaction, which is economically disadvantageous, and the yield may decrease due to a side reaction.

The above-mentioned reaction is carried out in the temperature range of generally 15° C.–100° C., preferably 20° C.–70° C. This is because, when the reaction temperature is less than 15° C., the reaction may proceed slowly, or the reaction may not proceed at all, and when the reaction temperature exceeds 100° C., carbonyl compound (i), which is a starting material, may be decomposed in the reaction mixture, or ester (ii), which is a resulting product, may be decomposed to possibly reduce the reaction yield. The above-mentioned reaction is generally carried out for 30 min–20 hr.

The solvent to be used for the above-mentioned reaction may be any as long as it does not inhibit the reaction, and ethers such as THF, dioxane, dimethoxyethane and the like, or a mixed solvent of such ethers and any selected from aromatic hydrocarbons, such as benzene, toluene, xylene and the like, and aliphatic hydrocarbons such as heptane, hexane, octane and the like, are preferably used. When a mixed solvent is to be used, they may be mixed at a conventionally known optional proportion.

The total amount of the solvent to be used is generally 100 mL–2000 mL per 1 mole of carbonyl compound (i), and for a smooth reaction and enhanced productivity of the reaction, it is preferably 150 mL–1500 mL.

In the above-mentioned method, by using 1-phenyl-3-hexanone [ketone (V)] as carbonyl compound (i) and setting various reaction conditions that are the same conditions as in said method, racemic 3-hydroxy-3-(2-phenylethyl)hexanoic acid ester [racemic carboxylic acid ester (VII)] can be obtained.

The racemic 3-hydroxy-3-(2-phenylethyl)hexanoic acid ester [racemic carboxylic acid ester (VII)] obtained in the above-mentioned step (a) can be isolated and purified by a conventional method. For example, the reaction mixture is poured into acidic water, and after partitioning, the organic layer is washed and filtrated. The obtained filtrate is washed, dried and concentrated under reduced pressure to isolate racemic carboxylic acid ester (VII). After isolation, for example, it may be subjected to silica gel column chromatography for purification. In addition, racemic carboxylic acid ester (VII) may be subjected to step (b) to be mentioned below without purification.

The ester (VI) to be used for the above-mentioned step (a) can be obtained by various conventionally known methods, or a commercially available one may be used.

The ketone (V) to be used for the above-mentioned step (a) can be produced according to a method described in US publication No. 2002/0013501A or a method comprising oxidization of 1-phenyl-3-hexanol with hypochlorite (JP-A-2002-265409), or a commercially available one can be used. However, one obtained by the following method proposed by the present inventors is preferable.

Production Method of 1-phenyl-3-hexanone (V)

1-Phenyl-3-hexanone [ketone (V)] can be obtained by condensing benzaldehyde of the formula (V-i) with 2-pentanone of the formula (V-ii) in the presence of a base as shown in the following reaction scheme to give propyl styryl ketone of the formula (V-iii), and then reducing the obtained propyl styryl ketone (V-iii).

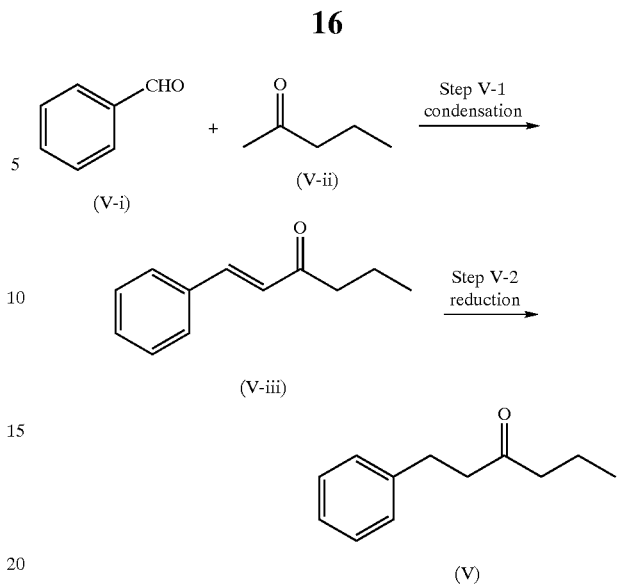

Each step is explained in the following.

Step V-1

This step is for obtaining propyl styryl ketone (V-iii) by condensing benzaldehyde (V-i) with 2-pentanone (V-ii).

In this condensation reaction, 2-pentanone (V-ii) is preferably used generally in a proportion of 1.1 mol–5.0 mol, but preferably in a proportion of 2.0 mol–3.5 mol, relative to 1 mol of benzaldehyde (V-i) in view of the reaction time.

The solvent to be used for this reaction is not subject to any particular limitation as long as it does not inhibit the reaction. Generally, a solvent such as water, primary or secondary alcohols (e.g., methanol, ethanol, isopropanol, etc.), tertiary alcohols (e.g., tert-butanol, tert-amyl alcohol, etc.), aromatic compound (e.g., toluene, monochlorobenzene, etc.), ethers (e.g., THF, dioxane, etc.), 2-pentanone, which is a starting material, and the like or a mixed solvents thereof are used. This solvent is preferably used in an amount of generally 50 mL–500 mL relative to 1 mole of benzaldehyde (V-i). From the economic aspect and smoothness of the reaction, it is 150 mL–400 mL. In the case of a mixed solvent, they are mixed at a conventionally known general proportion to make the total amount fall within the above-mentioned range.

The above-mentioned reaction is carried out in the presence of a base. Examples of the base include alkali metal hydroxide (sodium hydroxide, potassium hydroxide, etc.), alkali metal carbonate (sodium carbonate, potassium carbonate, sodium hydrogencarbonate, etc.), amine (triethylamine, etc.) and the like. Of these, alkali metal hydroxide is preferable. Particularly, sodium hydroxide and potassium hydroxide are preferable from the aspect of solubility in water. In addition, the amount of base to be used is generally 0.1 mol–1.0 mol relative to 1 mol of benzaldehyde (V-i). From the economic aspect and for the smooth progress of the reaction, it is preferably 0.2 mol–0.5 mol.

The above-mentioned reaction step is carried out generally at a temperature range of 40° C.–100° C. For sufficient reaction speed while suppressing a side reaction, a reaction in a temperature range of 55° C.–75° C. is preferable. This reaction is generally carried out in a reaction time of about 30 min–24 hr.

Step V-2

By reducing propyl styryl ketone (V-iii) obtained in the above-mentioned step V-1, 1-phenyl-3-hexanone (V) can be produced.

This reaction is generally carried out by adding a reduction catalyst to a solvent such as water, primary or secondary alcohols (e.g., methanol, ethanol, isopropanol, etc.), tertiary alcohols (e.g., tert-butanol, tert-amyl alcohol, etc.), aromatic compound (e.g., toluene, monochlorobenzene, etc.), esters (e.g., ethyl acetate, butyl acetate, etc.), ethers (e.g., THF, dioxane, etc.), ketones (e.g., acetone, methyl ethyl ketone) and the like, that do not inhibit the reaction or a mixed solvent thereof, preferably, ethyl acetate, THF, acetone or a mixed solvent thereof, and reacting propyl styryl ketone (V-iii) with hydrogen. It is also possible to use the reaction mixture after the above-mentioned step V-1 as a reaction solvent of this reduction reaction.

The reduction catalyst to be used for this reaction is exemplified by palladium carbon, palladium, palladium hydroxide, platinum oxide, platinum, platinum carbon, ruthenium oxide, ruthenium, ruthenium carbon and the like. Of these, palladium carbon and platinum oxide are preferable, and palladium carbon is particularly preferable. The amount of the reduction catalyst to be used is generally 2 g–20 g, preferably 4 g–10 g, relative to 1 mole of propyl styryl ketone (V-iii). When the amount of the reduction catalyst to be used is less than 2 g relative to 1 mole of propyl styryl ketone (V-iii), the reaction tends to become unpreferably slow, and when it exceeds 20 g, an effect corresponding to the amount to be used is not attained, which is economically unpreferable.

The amount of hydrogen to be used in this step is not particularly limited as long as it can reduce propyl styryl ketone (V-iii), and the reaction pressure is generally 50 kPa–1000 kPa, preferably 70 kPa–200 kPa, more preferably 90 kPa–150 kPa.

In this step, a base such as triethylamine, soda ash and the like may be added in an attempt to suppress a side reaction such as overreduction of 1-phenyl-3-hexanone (V), which is a product, and the like.

1-Phenyl-3-hexanone (V) [ketone (V)] obtained as above can be isolated by a conventional method. For example, the reduction catalyst is removed by filtration, and the filtrate is concentrated under reduced pressure to achieve isolation. The isolated ketone (V) can be purified by distillation under reduced pressure and the like. In addition, ketone (V) can be applied to the above-mentioned step (a) without purification.

Obtainment of ketone (V) to be used in the above-mentioned step (a) by the above-mentioned reaction is beneficial as compared to the method described in US publication 2002/0013501A and a method comprising oxidization of 1-phenyl-3-hexanol with hypochlorite (JP-A-2002-265409), because side reaction does not occur easily.

2. Step for Producing Racemic 3-hydroxy-3-(2-phenylethyl) hexanoic Acid [Step (b)]

This step is for producing 3-hydroxy-3-(2-phenylethyl) hexanoic acid [racemic carboxylic acid (II)] by hydrolysis of racemic 3-hydroxy-3-(2-phenylethyl)hexanoic acid ester [racemic carboxylic acid ester (VII)]. While the racemic carboxylic acid ester (VII) to be used for this step is not particularly limited, it is preferably obtained by the above-mentioned step (a).

The hydrolysis of the racemic carboxylic acid ester (VII) can be conducted according to a conventional method. For example, racemic carboxylic acid ester (VII) and alkali metal compound are reacted in a solvent to give a salt of racemic carboxylic acid (II), which is then neutralized with an acid as necessary to give racemic carboxylic acid (II).

The solvent to be used for step (b) may be, for example, methanol, ethanol, water and the like; or a mixed solvent thereof, preferably water.

The amount of the solvent to be used in step (b) is generally 1 L–10 L, preferably 1 L–5 L, per 1 kg of racemic carboxylic acid ester (VII).

The alkali metal compound to be used in step (b) is exemplified by sodium hydroxide and potassium hydroxide, with preference given to sodium hydroxide. The amount of the alkali metal compound to be used is generally 1.0 mole–10 moles, preferably 1.5 moles–2.5 moles, per 1 mole of racemic carboxylic acid ester (VII). When the amount of the alkali metal compound to be used is less than 1.0 mole relative to 1 mole of racemic carboxylic acid ester (VII), the reaction may not complete, which is unpreferable. When it is used in excess of 10 moles, an effect corresponding to the amount to be used is not attained, which is economically unpreferable. The alkali metal compound may be added to the reaction system as it is, but addition as an aqueous solution or alcohol solution is preferable. The amount of a solvent to be used for dissolving an alkali metal compound is included in the amount of the above-mentioned solvent to be used.

In step (b), the acid to be used for neutralization is exemplified by hydrochloric acid, sulfuric acid, phosphoric acid and the like and the amount of use thereof is such an amount as makes the pH of the reaction mixture generally not more than 7, preferably not more than 5.

In step (b), the reaction of the racemic carboxylic acid ester (VII) with an alkali metal compound depends on the kind of alkali metal compound and the amount thereof to be used and the like. The reaction is generally carried out at 15° C.–100° C., preferably 30° C.–60° C., and generally ends in 30 min–30 hr, preferably 1.5 hr–20 hr.

The racemic carboxylic acid (II) obtained in step (b) can be isolated and purified by a conventional method. For example, the reaction mixture is extracted with a solvent, washed and filtrated and the obtained filtrate is washed, dried and concentrated under reduced pressure to isolate racemic carboxylic acid (II).

The racemic carboxylic acid (II) obtained in step (b) is preferably used without purification, or as a solution of racemic carboxylic acid (II) leaving a part or the entirety of the extraction solvent in the isolation step, for step (c) to be mentioned below. That is, a solution of the extraction solvent of racemic carboxylic acid (II) obtained in step (b) is only partially concentrated and used in the following step (c) or used in (c) without concentration.

In this way, by using racemic carboxylic acid (II) as a solution leaving a part or the entirety of an extraction solvent in step (c) to be mentioned below, a step for concentration can be omitted, which is economically advantageous. In addition, a heat treatment for concentration can be avoided, and lower yield due to heat decomposition of racemic carboxylic acid (II) can be advantageously avoided.

As the extraction solvent, those used for optical resolution in step (c) to be mentioned below, such as one or more kinds of solvents selected from ethyl acetate, MIBK, methyl ethyl ketone, diisopropyl ether and THF, and the like are mentioned, with preference given to MIBK.

3. Step for Producing (R)-3-hydroxy-3-(2-phenylethyl) hexanoic Acid [Step (c)]

The step for producing (R)-3-hydroxy-3-(2-phenylethyl) hexanoic acid [(R)-carboxylic acid (III)] is characterized by the use of optically active amine of the formula

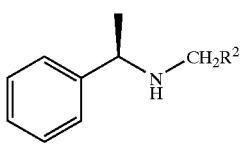

(VIII)

wherein R² is 3,4-dimethoxyphenyl or 2-chlorophenyl [optically active amine (VIII)], which is optically active, as an agent for the optical resolution of (R)-carboxylic acid (III) from racemic 3-hydroxy-3-(2-phenylethyl)hexanoic acid [racemic carboxylic acid (II)].

To be specific, the step is characterized by the use of (R)-N-(3,4-dimethoxybenzyl)-α-phenylethylamine of the following formula (VIIIa)

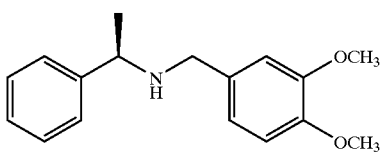

(VIIIa)

(hereinafter to be also referred to as "dimethoxy form (VIIIa)"), or (R)-N-(o-chlorobenzyl)-α-phenylethylamine of the following formula (VIIIb)

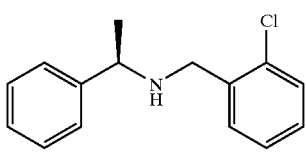

(VIIIb)

(hereinafter to be also referred to as "chloro form (VIIIb)"), as an agent for optical resolution.

In the following, dimethoxy form (VIIIa) and chloro form (VIIIb) may be simply referred to generally as "optically active amine (VIII)", without particular distinction.

According to such step (c), (R)-carboxylic acid (III) having an optical purity of not less than 97% e.e. can be obtained in the total yield of not less than 34% by the use of the above-mentioned optically active amine (VIII) as an agent for optical resolution. Particularly, when dimethoxy form (VIIIa) wherein R² is 3,4-dimethoxyphenyl is used, (R)-carboxylic acid (III) having not less than 99% e.e. can be obtained in the total yield of not less than 34%. As described above, the production method of the present invention can afford a salt of (R)-carboxylic acid (III) having the same level or high level of optical purity in the total yield of not less than about 1.3 fold, as compared to conventional optical resolution of (R)-carboxylic acid (III) using (−)-norephedrine. Such method strikingly improves industrial production efficiency of (R)-carboxylic acid (III) as compared to conventional cases.

As used herein, by "the total yield" is meant the yield (yield of the objective highly optically pure (R)-carboxylic acid (III) relative to racemic carboxylic acid (II)) throughout the reaction system, as mentioned above, which is to be distinguished from the yield in individual reactions in the reaction system (in the following, a simple reference to a "yield" means "a ratio of the amount of the resulting product actually produced from the starting material immediately before the reaction for producing the resulting product, relative to the theoretical amount of production of the resulting product").

As used herein, the optical purity is a value determined by high performance liquid chromatography (HPLC) to be mentioned below.

By this production method, racemic carboxylic acid (II) and the above-mentioned optically active amine (VIII) are specifically mixed in a solvent to allow crystallization (crystal precipitation) to give a salt of (R)-carboxylic acid (III) with optically active amine. The racemic carboxylic acid (II) to be used for this step is not particularly limited, but one produced by the above-mentioned step (b) is preferable.

The racemic carboxylic acid (II) and the optically active amine (VIII) are preferably mixed at a ratio of 1:0.5–1:1 (molar ratio), more preferably 1:0.8–1:1 (molar ratio), to economically achieve higher yield and higher optical purity. When the amount of optically active amine (VIII) to be used is less than 0.5 mole relative to 1 mole of racemic carboxylic acid (II), the optical purity tends to increase, but the yield tends to unpreferably decrease. When the amount of optically active amine (VIII) to be used exceeds 1 mole relative to 1 mole of racemic carboxylic acid (II), filtration property of the salt tends to be degraded. In addition, yield and optical purity do not show any particular changes, which is economically unpreferably useless.

The solvent to be used for the above-mentioned mixing of racemic carboxylic acid (II) and optically active amine (VIII) is exemplified by one or more kinds of solvents selected from ethyl acetate, methanol, isopropanol, ethanol, acetonitrile, MIBK, acetone, methyl ethyl ketone, diisopropyl ether, dimethoxyethane and THF. These solvents may further contain water. From the aspects of the yield and optical purity of the salt, and safety, one or more kinds of the solvents selected from ethyl acetate, methanol, isopropanol, ethanol, MIBK, diisopropyl ether and THF from among the above-mentioned are particularly preferable. Moreover, from the aspect of the extraction solvent in the above-mentioned step (b), one or more kinds of solvents selected from ethyl acetate, MIBK, methyl ethyl ketone, diisopropyl ether and THF, particularly MIBK, are particularly preferable. The use of these solvents further containing water is preferable.

As mentioned above, as the solvent to be used for the above-mentioned mixing of racemic carboxylic acid (II) and the above-mentioned optically active amine (VIII), a part or the entirety of the extraction solvent of the above-mentioned step (b) is preferably left and used. That is, a part or the entirety of the extraction solvent for racemic carboxylic acid (II) obtained in the above-mentioned step (b) is left upon partially concentration or without concentration, and the optical resolution is preferably conducted in the solvent containing the above-mentioned solvent as necessary.

The amount of the above-mentioned solvent to be used is free of any particular limitation. For a salt to be obtained in a higher yield with a higher optical purity, it is preferably 5 L–20 L, more preferably 8 L–16 L, relative to 1 kg of racemic carboxylic acid (II). When the amount of the solvent to be used is less than 5 L relative to 1 kg of racemic carboxylic acid (II), heating during production of the salt may fail to dissolve the resulting salt, which unpreferably lowers the optical purity. When the amount of the solvent to be used exceeds 20 L relative to 1 kg of racemic carboxylic acid (II), the amount of the salt that dissolves in the solvent tends to increase and lower the yield, which is unpreferable.

When the above-mentioned solvent is a mixed solvent (inclusive of a mixture with water), the solvents are mixed in a conventionally known general and optional ratio to achieve the above-mentioned ranges of the amounts to be used. When the racemic carboxylic acid (II) is used as a solution of an extraction solvent of the above-mentioned step (b), the amount of the extraction solvent is included in the amount of the solvent to be used for optical resolution.

The aforementioned racemic carboxylic acid (II) and optically active amine (VIII) are mixed by adding optically active amine (VIII) to a solution of racemic carboxylic acid (II) dissolved in advance in a general solvent or a solution of the extraction solvent in step (b). Stirring the mixture after the addition results in the precipitation of the salt. Therefore, the mixture is generally heated to 50° C.–100° C. and stirred to dissolve the salt. When dissolution of the salt is insufficient by stirring at the raised temperature, the solvent may be further added until the salt is dissolved. The solvent to be further added here is similar to the aforementioned solvents.

The crystallization of a salt of (R)-carboxylic acid (III) with optically active amine (VIII) includes stirring with cooling until the salt is precipitated after the above-mentioned stirring at a raised temperature. Then, the mixture is gradually cooled, and after stirring further at a given temperature (e.g., 25° C.), the mixture is filtrated, washed with a solvent and stirred to give a highly optically pure amine salt of (R)-carboxylic acid (III) in the aforementioned yield.

During stirring with cooling until the salt is sufficiently precipitated, the crystal precipitation temperature is generally not more than 50° C., preferably 0° C.–30° C., and the stirring time is generally 0.5 hr–20 hr.

The solvent to be used after filtration is preferably a solvent having the solvent composition used for crystal precipitation. The amount of the solvent to be used for washing is not particularly limited and is an amount sufficient for washing the filtrate.

The production method of the present invention may be realized by gradually adding a solution of optically active amine (VIII) to a solution of racemic carboxylic acid (II) at room temperature (20° C.)-50° C. to allow gradual precipitation of the salt, and allowing the mixture to cool. By this method, the amount of the solvent to be used can be advantageously reduced as compared to the above-mentioned method, because the salt does not need to be dissolved completely once.

For recrystallization, the solvent to be used for dissolving a salt of (R)-carboxylic acid (III) can be similar to that used for dissolving racemic carboxylic acid (II) in the above-mentioned optical resolution, wherein the preferable solvent is the same. The amount of these solvents to be used for this reaction is free of any particular limitation, but it is preferably 4 L–20 L, more preferably 5 L–15 L, particularly preferably 8 L–15 L, relative to 1 kg of a salt of (R)-carboxylic acid (III), because high yield and high optical purity can be achieved. When the amount of the above-mentioned solvent to be used is less than 4 L relative to 1 kg of a salt of (R)-carboxylic acid (III), the salt may be difficult to dissolve, unpreferably making high optical purity difficult to achieve and stirring for cooling also difficult. When it exceeds 20 L, the amount of the dissolved salt tend to increases to unpreferably cause lower yield.

After mixing a salt of (R)-carboxylic acid (III) with the above-mentioned solvent, the mixture is generally heated to a temperature range of 50° C.–100° C. to dissolve the salt.

After dissolution of the salt of (R)-carboxylic acid (III), this solution is gradually cooled and seed crystals are added at a suitable temperature (e.g., 40° C.–80° C.), followed by stirring. The time of the stirring is generally about 10 min–5 hr. Further, the mixture is gradually generally cooled to 0° C.–40° C., preferably 0° C.–30° C., over 60 min–24 hr.

Then, the mixture is stirred further at a given temperature (e.g., 25° C.), filtrated, washed with a solvent and dried. The solvent to be used for filtration and washing is desirably similar to that used for crystal precipitation. The obtained filtrate may be mixed with the aforementioned salt of optically active amine (VIII) with racemic carboxylic acid (II) and used again for optical resolution.

The obtained amine salt of (R)-carboxylic acid (III) can be decomposed into (R)-carboxylic acid (III) and optically active amine (VIII) by a conventional method. For example, amine salt of (R)-carboxylic acid (III) is decomposed in an organic solvent (e.g., ethyl acetate, etc.) with, for example, aqueous caustic alkali solution, aqueous alkali carbonate solution or aqueous sodium bicarbonate, leaving the optically active amine in the organic layer, and using, for example, an inorganic acid such as hydrochloric acid, sulfuric acid and the like, the aqueous layer is made acidic and extracted with an organic solvent to give (R)-carboxylic acid (III).

Alternatively, an amine salt of (R)-carboxylic acid (III) may be decomposed with aqueous acid solution (e.g., inorganic acid such as hydrochloric acid, sulfuric acid etc., and the like) in an organic solvent (e.g., toluene, ethyl acetate, MIBK, or a mixed solvent of these with heptane) and extracted with the organic solvent to give (R)-carboxylic acid (III). In this case, optically active amine (VIII) can be obtained as an aqueous salt solution of the acid used for the above-mentioned decomposition of the amine salt.

The optically active amine (VIII) used for optical resolution is preferably recovered from the mother liquor of the optical resolution or crystal salt of (R)-carboxylic acid (III) with optically active amine (VIII) (hereinafter to be also referred to as "salt with carboxylic acid and the like").

As used herein, the recovery from the mother liquor of the optical resolution means a recovery of optically active amine (VIII) from a salt of (S) rich carboxylic acid (II) with optically active amine (VIII).

Furthermore, the recovery from a salt of (R)-carboxylic acid (III) with optically active amine (VIII) means a recovery of optically active amine (VIII) produced by the decomposition of a salt of (R)-carboxylic acid (III) with optically active amine (VIII).

A method for recovering optically active amine (VIII) from a salt with carboxylic acid and the like may be a conventional method. For example, a filtrate-washing mixture containing a salt of (S) rich 3-hydroxy-3-(2-phenylethyl)hexanoic acid with optically active amine (VIII) or a salt of (R)-carboxylic acid (III) with optically active amine (VIII) is decomposed with aqueous caustic alkali solution, aqueous alkali carbonate solution or aqueous sodium bicarbonate in an organic solvent (e.g., toluene, ethyl acetate, MIBK, or a mixed solvent of these with heptane) to recover optically active amine (VIII) as a solution in an organic solvent layer.

In addition, a filtrate-washing mixture containing a salt of (S) rich 3-hydroxy-3-(2-phenylethyl)hexanoic acid with optically active amine (VIII) or a salt of (R)-carboxylic acid (III) with optically active amine (VIII) is decomposed with an aqueous acid solution (e.g., inorganic acid such as hydrochloric acid, sulfuric acid etc., and the like) in an organic solvent (e.g., toluene, ethyl acetate, MIBK, or a mixed solvent of these with heptane) to recover an aqueous acid solution of optically active amine (VIII) with the acid used for the above-mentioned decomposition of the amine salt. Moreover, after treatment of the aqueous layer with aqueous caustic alkali solution, aqueous alkali carbonate solution or aqueous sodium bicarbonate and the like, it is extracted with an organic solvent (e.g., toluene, ethyl acetate, MIBK, or a mixed solvent of these with heptane) to give optically active amine (VIII) solution of an organic solvent.

The recovered optically active amine (VIII) can be isolated and purified by a conventional method. For example, an organic solvent layer containing the optically active amine (VIII) is washed with water and concentrated to isolate optically active amine (VIII). After isolation, it is purified by distillation under reduced pressure or the recovered optically active amine (VIII) solution of an organic solvent may be subjected to optical resolution without purification.

Using the optically active amine (VIII) recovered as mentioned above, the optically active amine (VIII) can be used repeatedly and the process is economical than new synthesis. Therefore, (R)-carboxylic acid (III) can be produced at a lower cost.

The (R)-3-hydroxy-3-(2-phenylethyl)hexanoic acid [(R)-carboxylic acid (III)] obtained as above is considered to be extremely useful as a synthetic intermediate for the anti-HIV agent, PNU-140690. The derivatization from (R)-carboxylic acid (III) into PNU-140690 can be done as described in, for example, the above-mentioned reference (J. Org. Chem., Vol. 63, No. 21, 1998, 7348–7356).

In addition, (R)-5-hydroxy-3-oxo-5-(2-phenylethyl) octanoic acid ester can be produced by the method proposed below by the present inventors using (R)-carboxylic acid (III).

Production Method of Optically Active Amine (VIII)
(i) Method 1

The optically active amine (VIII) to be used in the above-mentioned step (c) is preferably obtained by the following method proposed by the present inventors.

That is, as shown in the following scheme, a compound of the formula (VIII-i) (hereinafter to be also referred to as "compound (VIII-i)") and (R)-1-phenylethylamine of the formula (VIII-ii) (hereinafter to be also referred to as "(R)-amine (VIII-ii)") are condensed to give an imine compound of the formula (VIII-iii) (hereinafter to be also referred to as "imine compound (VIII-iii)") (step VIII-1), after which it is reduced (step VIII-2) to give optically active amine (VIII).

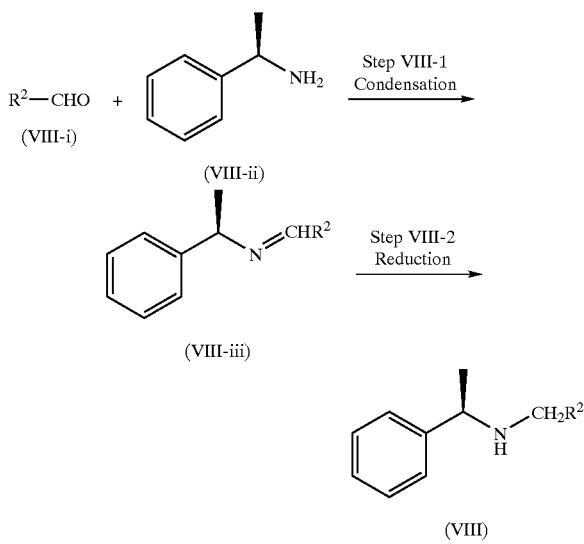

wherein $R^2$ is as defined above.

The production method of optically active amine (VIII) is explained in the following.

The imine compound (VIII-iii) in the above-mentioned reaction can be obtained by condensation of compound (VIII-i) and (R)-amine (VIII-ii) (step VIII-1). In this condensation reaction, (R)-amine (VIII-ii) is generally used in an amount of 80 mol %–100 mol %, preferably 90 mol %–100 mol %, of compound (VIII-i).

The solvent in step VIII-1 is not subject to any particular limitation as long as it does not inhibit the reaction. Generally, methanol, ethanol, isopropanol, toluene and the like, preferably methanol, isopropanol, toluene and the like or a mixed solvent thereof are used. The above-mentioned solvent is generally used in an amount of 100 mL–500 mL relative to 1 mole of compound (VIII-i), which is preferably 200 mL–400 mL from the economic aspect and for the smooth progress of the reaction. In the case of a mixed solvent, they are mixed at a conventionally known general proportion to make the total amount fall within the above-mentioned range.

The step VIII-1 is carried out generally in a temperature range of 25° C.–80° C. For sufficient reaction speed while suppressing a side reaction, a reaction in a temperature range of 30° C.–60° C. is preferable. This reaction is generally carried out in a reaction time of about 15 min–10 hr.

The imine compound (VIII-iii) thus obtained is reduced to give optically active amine (VIII) (step VIII-2). This reaction is generally carried out by adding a reduction catalyst to the hydrogenation reaction mixture after the above-mentioned step VIII-1 to allow hydrogenation reaction of imine compound (VIII-iii) with hydrogen to give the optically active amine (VIII).

The reduction catalyst is exemplified by palladium carbon, palladium, palladium hydroxide, platinum oxide, platinum, platinum carbon, ruthenium oxide, ruthenium, ruthenium carbon and the like. Preferred are palladium carbon and platinum oxide, and more preferred is palladium carbon. The amount of the reduction catalyst to be used is generally 1 g–10 g, preferably 1.5 g–5.0 g, relative to 1 mole of compound (VIII-i). When the amount of the reduction catalyst to be used is less than 1 g relative to 1 mole of compound (VIII-i), the reaction tends to become unpreferably slow, and when it exceeds 10 g, an effect corresponding to the amount to be used is not attained, which is economically unpreferable.

The amount of the hydrogen to be used in step VIII-2 is no particularly limited as long as it can reduce the imine compound (VIII-iii). The reaction pressure is generally 100 kPa–3000 kPa, preferably 100 kPa–2000 kPa, more preferably 200 kPa–1500 kPa.

In step VIII-2, a base such as triethylamine, soda ash and the like is preferably added to suppress a side reaction such as hydrogenolysis of optically active amine (VIII), and the like. The amount of the base to be added is generally 0.1 g–10 g, preferably 1 g–3 g, relative to 1 g of the reduction catalyst. When the amount of the base is less than 0.1 g relative to 1 g of the reduction catalyst, side reaction such as hydrogenolysis of optically active amine (VIII) and the like unpreferably may not be sufficiently suppressed. When it exceeds 10 g, the reduction catalyst is possibly inactivated to make the reaction slow, which is unpreferable.

The recovered optically active amine (VIII) obtained in step VIII-2 can be isolated and purified by a conventional method. For example, a reduction catalyst is removed by filtration and then the filtrate is concentrated under reduced pressure for isolation. The isolated optically active amine (VIII) can be purified by distillation under reduced pressure and the like. The optically active amine (VIII) may be subjected to the above-mentioned step (c) without purification.

The above-mentioned reduction during production of optically active amine (VIII) used in the above-mentioned step (c) is economical as compared to reduction using a reducing agent such as sodium borohydride and the like, because a reducing agent does not need to be used in a stoichiometric amount and the reduction catalyst can be used repeatedly. In addition, complicated manipulation such as decomposition of the reducing agent and the like is not necessary and a convenient operation of filtration of the reduction catalyst and concentration of filtrate is sufficient, thus advantageously making the step efficient.

(ii) Method 2

The dimethoxy form (VIIIa) [(R)-N-(3,4-dimethoxybenzyl)-α-phenylethylamine] of the optically active amine (VIII) used in step (c) of the present invention can be also obtained as in the following.

First, (R)-1-phenylethylamin is added while heating 3,4-dimethoxybenzaldehyde solution to about 40° C.–60° C. The solvent to dissolve 3,4-dimethoxybenzaldehyde is free of particular limitation and exemplified by methanol, isopropanol, ethanol and the like. It is preferable that the amount of (R)-1-phenylethylamine to be added is in a proportion of 90 mol %–100 mol % of 3,4-dimethoxybenzaldehyde.

After the addition of (R)-1-phenylethylamine, the mixture is stirred with heating for about 0.5 hr–2 hr and cooled to 20° C.–35° C., after which sodium borohydride is added. In view of the reactivity, sodium borohydride is preferably added in a proportion of about 1:0.5 (molar ratio) relative to 1 mole of 3,4-dimethoxybenzaldehyde.

After the above-mentioned reaction, the mixture is extracted with toluene and the like, washed and concentrated by a method known per se to give (R)-N-(3,4-dimethoxybenzyl)-α-phenylethylamine.

A chloro form (VIIIb)[(R)-N-(o-chlorobenzyl)-α-phenylethylamine] of the optically active amine (VIII) can be obtained in the same manner as in the aforementioned synthetic method of dimethoxy form (VIIIa) except that 2-chlorobenzaldehyde is used instead of 3,4-dimethoxybenzaldehyde.

4. Production Method of (R)-5-hydroxy-3-oxo-5-(2-phenylethyl)octanoic Acid Ester This method is, as shown in the following scheme, a production method comprising reacting (R)-3-hydroxy-3-(2-phenylethyl)hexanoic acid [(R)-carboxylic acid (III)], a halogenating agent and an imidazole compound of the formula (iv) (hereinafter to be also referred to as "imidazole compound (iv)") in the presence of a base to give an imidazolide of the formula (IX) (hereinafter to be also referred to as "imidazolide (IX)"), which imidazolide (IX) obtained is reacted with malonic acid monoester of the formula (v) (hereinafter to be also referred to as "malonic acid monoester (v)") in the presence of a divalent metal salt and treated with an acid to give (R)-5-hydroxy-3-oxo-5-(2-phenylethyl)octanoic acid ester of the formula (X) (hereinafter to be also referred to as "(R)-carboxylic acid ester (X)"). The (R)-carboxylic acid (III) to be used for this method is not particularly limited and one obtained according to the method described in J. Org. Chem., Vol. 63, No. 21, 1998, p7348–7356 and the like, with preference given to one produced by the above-mentioned step (c).

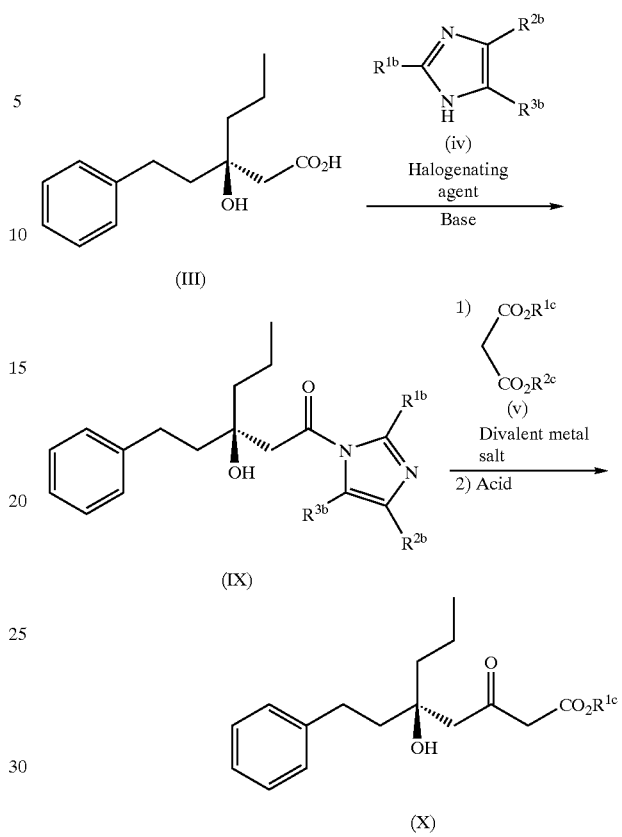

wherein $R^{1b}$, $R^{2b}$ and $R^{3b}$ are the same or different and each is hydrogen atom or organic group, and $R^{1c}$ and $R^{2c}$ are free of particular limitation as long as they do not influence the reaction.

This method can be applied to a produce method β-ketoester other than (R)-carboxylic acid ester (X) from a carboxylic acid other than (R)-carboxylic acid (III). The production method is explained in the following including the production of β-ketoester other than (R)-carboxylic acid ester (X).

As shown in the following scheme, carboxylic acid of the formula (vi) (hereinafter to be also referred to as "carboxylic acid (vi)") such as (R)-carboxylic acid (III), a halogenating agent and an imidazole compound (iv) are reacted in the presence of a base to give imidazolide of the formula (vii) (hereinafter to be also referred to as "imidazolide (vii)") and the obtained imidazolide (vii) is reacted with malonic acid monoester (v) in the presence of a divalent metal salt, and treat with an acid to give β-ketoester of the formula (viii) (hereinafter to be also referred to as "β-ketoester (viii)"), such as (R)-carboxylic acid ester (X). The β-ketoester (viii) obtained by this method is a useful intermediate for a pharmaceutical product, pesticide and the like.

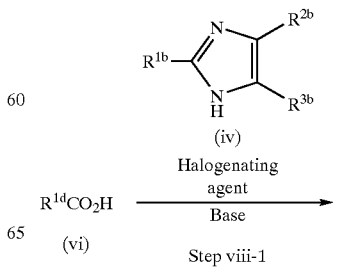

Step viii-1

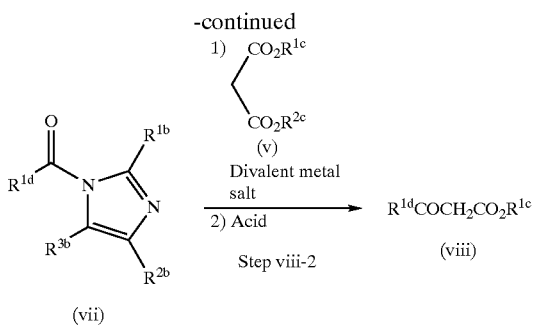

wherein $R^{1d}$ is an organic group and $R^{1b}$, $R^{2b}$, $R^{3b}$, $R^{1c}$ and $R^{2c}$ are as defined above.

The "organic group" for $R^{1d}$ of the formula (vi) in the above-mentioned production method is exemplified by alkyl group optionally having substituents, cycloalkyl group optionally having substituents, aryl group optionally having substituents, aralkyl group optionally having substituents, heteroaryl group optionally having substituents and the like.

As the "alkyl group" of the above-mentioned "alkyl group optionally having substituents", straight or branched chain alkyl group having 1–20 carbon atoms is mentioned. Examples thereof include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like. Preferably, straight or branched chain alkyl group having 1–12 carbon atoms, such as, ethyl, heptyl, heptadecyl, 3-heptyl and the like can be mentioned. The alkyl group may have a double bond or a triple bond, and examples thereof include allyl, propinyl and the like.

The "cycloalkyl group" of the above-mentioned "cycloalkyl group optionally having substituents" is exemplified by cycloalkyl group having 3–8 carbon atoms, such as cyclopropyl, cyclobutyl, cyclopentyl, cyclohexyl, cycloheptyl, cyclooctyl and the like. Preferably, cycloalkyl group having 3–6 carbon atoms, such as, cyclopropyl, cyclohexyl and the like can be mentioned.

The "aryl group" of the above-mentioned "aryl group optionally having substituents" is exemplified by aryl group having carbon atoms 6–18, such as, phenyl, 1-naphthyl, 2-naphthyl, 1-anthryl, 2-anthryl, 9-anthryl and the like. Preferably, aryl group having carbon atoms 6–12, such as phenyl, 2-naphthyl and the like can be mentioned.

As regards "aralkyl group" of the above-mentioned "aralkyl group optionally having substituents", aralkyl group having 7–20 carbon atoms can be mentioned, wherein the aryl moiety is the same as the above-mentioned "aryl group", and the alkyl moiety is a straight or branched chain alkyl group having 1–14 carbon atoms. Examples thereof include benzyl, 1-phenethyl, 2-phenylethyl, 2-(2-phenylethyl)pentyl and the like. Preferred is aralkyl group having 7–16 carbon atoms, such as, 2-phenylethyl, 2-(2-phenylethyl)pentyl and the like. The alkyl moiety of this aralkyl group may have a double bond or triple bond, and examples of such aralkyl group include styryl and the like.

The "heteroaryl group" of the above-mentioned "heteroaryl group optionally having substituents" is exemplified by a 5-membered-13-membered heteroaryl ring having one or more hetero atoms selected from the group consisting of nitrogen atom, sulfur atom and oxygen atom and 3–12 carbon atoms. Examples thereof include pyridyl, quinolyl, isoquinolyl, thienyl, furyl, oxazolyl, thiazolyl, imidazolyl, pyrimidinyl, pyrazinyl and the like, with preference given to 6-membered-13-membered heteroaryl ring group having one nitrogen atom and 5–9 carbon atoms, such as, pyridyl, quinolyl and the like.

These groups may have a substituent that does not inhibit this reaction, such as hydroxyl group, halogen atom (e.g., chlorine atom, fluorine atom, bromine atom, iodine atom, etc.), alkoxy group having 1–6 carbon atoms (e.g., methoxy, ethoxy, propoxy, butoxy, pentyloxy, hexyloxy, etc.), alkoxycarbonyl group having 2 to 8 carbon atoms (e.g., methoxycarbonyl, ethoxycarbonyl, propoxycarbonyl, butoxycarbonyl, pentyloxycarbonyl, hexyloxycarbonyl, heptyloxycarbonyl, etc.), nitro group, oxo group, nitrile group, amide group having 1–8 carbon atoms (e.g., formamide, acetamide, propionamide, butylamide, pentaneamide, hexaneamide, heptanamide, octaneamide, benzamide, etc.), as well as the above-defined "alkyl group", "cycloalkyl group", "aryl group", "aralkyl group" and "heteroaryl group" and the like. While the number of the substituent is not particularly limited, but it is preferably 1–3, which may be the same or different.

Preferable examples of carboxylic acid (vi) in the above-mentioned production method are shown in the following.

(1) The carboxylic acid having the above-mentioned "alkyl group optionally having substituents" is exemplified by propionic acid, capric acid, stearic acid, 2-ethylhexanoic acid and the like.

(2) The carboxylic acid having the above-mentioned "cycloalkyl group optionally having substituents" is exemplified by, cyclopropanoic acid, cyclohexanoic acid and the like.

(3) The carboxylic acid having the above-mentioned "aryl group optionally having substituents" is exemplified by benzoic acid, 4-hydroxybenzoic acid, naphthalene-2-carboxylic acid, 4-chlorobenzoic acid and the like.

(4) The carboxylic acid having the above-mentioned "aralkyl group optionally having substituents" is exemplified by 3-phenylpropionic acid, 2-cyclohexyl-2-hydroxy-2-phenylacetic acid, cinnamic acid, 3-(2-phenylethyl)hexanoic acid, 3-hydroxy-3-(2-phenylethyl)hexanoic acid and the like.

(5) The carboxylic acid having the above-mentioned "heteroaryl group optionally having substituents" is exemplified by 2-chloronicotinic acid, 2,6-dichloro-5-fluoronicotinic acid, quinoline-3-carboxylic acid and the like.

Of these, 3-hydroxy-3-(2-phenylethyl)hexanoic acid (particularly an (R) isomer thereof), 2,6-dichloro-5-fluoronicotinic acid, cinnamic acid, 4-hydroxybenzoic acid and the like are preferable because they can produce β-ketoester useful as an intermediate for a pharmaceutical agent.

The "imidazole compound" in the above-mentioned production method refers to a compound wherein the hydrogen atom bonded to the carbon of imidazole is optionally substituted by an organic group, such as, imidazole, 2-methylimidazole and the like, with preference given to imidazole.

The "organic group" for $R^{1b}$, $R^{2b}$ and $R^{3b}$ of the above-mentioned formula (iv) is exemplified by alkyl group, cycloalkyl group, aryl group, aralkyl group and the like.

As the aforementioned "alkyl group", straight or branched chain alkyl having 1–6 carbon atoms, such as methyl, ethyl, propyl, isopropyl, butyl, isobutyl, sec-butyl, tert-butyl, pentyl, isopentyl, neopentyl, hexyl and the like can be mentioned.

The aforementioned "cycloalkyl group" is exemplified by cycloalkyl group having 3–6 carbon atoms, such as, cyclopropyl, cyclobutyl, cyclopentyl and the like.

The aforementioned "aryl group" is exemplified by phenyl, naphthyl, tolyl, xylyl, mesityl, cumenyl and the like.

The aforementioned "aralkyl group" is exemplified by benzyl, phenethyl, phenylpropyl and the like.

The aforementioned "halogenating agent" is not particularly limited and is exemplified by thionyl chloride, thionyl bromide, phosgene, diphosgene, triphosgene and the like, with preference given to thionyl chloride.

The "base" in the above-mentioned method is exemplified by aliphatic tertiary amines (e.g., trimethylamine, triethylamine, tributylamine, diisopropylethylamine and the like), aromatic tertiary amines (e.g., pyridine, picoline, 2,6-lutidine, collidine, 4-(N,N-dimethylamino)pyridine, N,N-dimethylaniline, N,N-diethylaniline and the like) or alkali metal carbonate (e.g., sodium carbonate, potassium carbonate and the like). Preferred is triethylamine or sodium carbonate and particularly preferred is triethylamine.

The "malonic acid monoester (v)" to be used for the above-mentioned method is free of particular limitation and is exemplified by malonic acid monoalkylester, or a compound of the formula (v) wherein $R^{1c}$ is straight or branched chain alkyl group having 1–6 carbon atoms (e.g., methyl, ethyl, isopropyl, n-butyl, isobutyl, sec-butyl, tert-butyl, pentyl, isopentyl, neopentyl, hexyl, etc.), preferably straight or branched chain alkyl group having 1–4 carbon atoms (e.g., ethyl, isopropyl, tert-butyl, etc.) and $R^{2c}$ is hydrogen atom or monovalent metal atom, preferably, alkali metal atom (e.g., sodium, potassium, etc.). Specifically, potassium ethyl malonate, sodium ethyl malonate, potassium isopropyl malonate, potassium tert-butyl malonate and the like are mentioned. In view of easiness of obtainment, potassium ethyl malonate is preferably used.

The "divalent metal salt" in the above-mentioned method is preferably magnesium chloride.

The "acid" in the above-mentioned method is exemplified by mineral acids (e.g., hydrochloric acid, hydrobromic acid, sulfuric acid, nitric acid, phosphoric acid and the like), organic acids (e.g., acetic acid, propionic acid, methanesulfonic acid, toluenesulfonic acid and the like) and the like, with preference given to hydrochloric acid.

In the above-mentioned method, by "treated with an acid" is meant addition of an acid to a reaction mixture or addition of a reaction mixture to an acid to changing the liquid property of the reaction mixture from neutral to weak acidic.

Step viii-1

A reaction to produce imidazolide (vii) is realized by reacting carboxylic acid (vi), a halogenating agent and imidazole compound (iv) in a solvent in the presence of a base.

In the above-mentioned reaction, the order of addition of reagents is not particularly limited and, for example, halogenating agent is added to a mixture of imidazole compound (iv) and carboxylic acid (vi) charged in a solvent in advance in the presence of a base; after adding a halogenating agent to imidazole compound (iv) charged in a solvent in the presence of a base, carboxylic acid (vi) is further added; or after adding a mixture of a base and imidazole compound (iv) to a halogenating agent charged in a solvent, carboxylic acid (vi) is further added and the like.

In the above-mentioned reaction, the amount of imidazole compound (iv) to be used is preferably 1 mole–3 moles relative to 1 mole of carboxylic acid (vi), which is more preferably 1.1 moles–2.2 moles from the economic aspect. In the above-mentioned reaction, when the amount of imidazole compound (iv) to be used is less than 1 mole relative to 1 mole of carboxylic acid (vi), reaction efficiency may reduce because carboxylic acid (vi) remains partly unreacted. In the above-mentioned reaction, the use of imidazole compound (iv) in excess of 3 moles relative to 1 mole of carboxylic acid (vi) is economically unpreferable because imidazole compound (iv) not involved in the reaction exists in a large amount.

In the above-mentioned reaction, the amount of the halogenating agent to be used is preferably 1 mole–1.1 moles relative to 1 mole of carboxylic acid (vi), which is more preferably 1.01 moles–1.05 moles from the economic aspect. In the above-mentioned reaction, when the amount of halogenating agent to be used is less than 1 mole relative to 1 mole of carboxylic acid (vi), the reaction efficiency may reduce because carboxylic acid (vi) remains partly unreacted. In the above-mentioned reaction, when the amount of halogenating agent to be used exceeds 1.1 moles relative to 1 mole of carboxylic acid (vi), a large amount of halogenating agent unnecessary for the reaction with carboxylic acid (vi) is used, which is not only economically unpreferable but may cause side reaction such as dehydrating reaction, elimination reaction and the like, because halogenating agent remains in the resulting product.

In the above-mentioned reaction, the amount of base to be used is preferably 1 mole–3 moles relative to 1 mole of carboxylic acid (vi), which is more preferably 1.1 moles–2.5 moles from the economic aspect. In the above-mentioned reaction, when the amount of base to be used is less than 1 mole relative to 1 mole of carboxylic acid (vi), the reaction efficiency may reduce because carboxylic acid (vi) remains partly unreacted. In addition, the reaction mixture may become acidic and the side reaction such as dehydrating reaction, elimination reaction and the like may be caused. In the above-mentioned reaction, moreover, when the amount of base to be used exceeds 3 moles relative to 1 mole of carboxylic acid (vi), a large amount of base unnecessary for the reaction with carboxylic acid (vi) is used, which is economically unpreferable.

The above-mentioned reaction is carried out generally within a temperature range of $-25°$ C.–$0°$ C., preferably $-20°$ C.–$-10°$ C. When the reaction temperature is less than $-25°$ C., the reaction may proceed slowly, or the reaction may not proceed at all, and when the reaction temperature exceeds $0°$ C., carboxylic acid (vi), which is a starting material, may be decomposed in the reaction mixture, or imidazolide (vii), which is a resulting product, may be decomposed to reduce the reaction yield.

The reaction time of the above-mentioned reaction is not particularly limited and the reaction completes generally in 30 min–1 hr.

The solvent to be used for the above-mentioned reaction may be any as long as it does not inhibit the reaction and ethers such as THF, dioxane, dimethoxyethane and the like, or a mixed solvent of the ethers with any solvent selected from aromatic hydrocarbons such as benzene, toluene, xylene and the like, aliphatic hydrocarbons such as heptane, hexane, octane and the like can be preferably used. In the case of a mixed solvent, they are mixed at a conventionally known general proportion to make the total amount fall within the above-mentioned range.

The amount of the solvent to be used is generally 800 mL–4500 mL relative to 1 mole of carboxylic acid (vi), which is preferably 1000 mL–3000 mL for the smooth progress of the reaction and enhanced productivity.

Imidazolide (vii) can be isolated and purified by a known isolation method (e.g., extraction, drying and the like) and by a known purification method (e.g., crystallization and the like), or may be used as it is in a reaction mixture without isolation and purification.

Step viii-2

Imidazolide (vii) obtained as mentioned above, for example, is reacted with malonic acid monoester (v) in a solvent in the presence of a divalent metal salt [step viii-2-1], and treated with an acid [step viii-2-2] to give β-ketoester (viii).

Step viii-2-1

In this step, the order of addition of reagents is not particularly limited and, for example, imidazolide (vii) is added to a mixture of malonic acid monoester (v) and divalent metal salt charged in a solvent in advance or malonic acid monoester (v) is added to a mixture of imidazolide (vii) and divalent metal salt charged in a solvent in advance and the like.

In this step, the amount of malonic acid monoester (v) to be used is preferably 1 mole–2 moles relative to 1 mole of imidazolide (vii), which is more preferably 1.3 moles–1.6 moles from the economic aspect. In the above-mentioned step viii-2-1, when the amount of malonic acid monoester (v) to be used is less than 1 mole relative to 1 mole of imidazolide (vii), the reaction efficiency may reduce because imidazolide (vii) remains partly unreacted. In the above-mentioned step viii-2-1, the use of malonic acid monoester (v) in excess of 2 moles relative to 1 mole of imidazolide (vii) is economically unpreferable because malonic acid monoester (v) not involved in the reaction exists in a large amount.

In this step, the amount of divalent metal salt to be used is preferably 1 mole–2 moles relative to 1 mole of malonic acid monoester (v), which is more preferably 1.1 moles–1.5 moles from the economic aspect. In the above-mentioned step viii-2-1, when the amount of divalent metal salt to be used is less than 1 mole relative to 1 mole of malonic acid monoester (v), the reaction efficiency may reduce because malonic acid monoester (v) remains partly unreacted. In the above-mentioned step viii-2-1, the use of divalent metal salt in excess of 2 moles relative to 1 mole of malonic acid monoester (v) is economically unpreferable, because a large amount of divalent metal salt not necessary for the reaction with malonic acid monoester (v) is present.

This step is carried out generally within a temperature range of 20° C.–70° C., preferably 40° C.–60° C. When the reaction temperature is less than 20° C., the reaction may proceed slowly, or the reaction may not proceed at all, and when the reaction temperature exceeds 70° C., imidazolide (vii), which is a starting material, may be decomposed in the reaction mixture to reduce the reaction yield.

The reaction time of the above-mentioned reaction is not particularly limited and the reaction completes generally in 4 hr–10 hr.

Step viii-2-2

In this step, an acid may be added to the reaction mixture in the above-mentioned step viii-2-1, or the reaction mixture in step viii-2-1 may be added to an acid.

In this step, the amount of the acid is preferably 2 moles–4 moles relative to 1 mole of imidazolide (vii), which is more preferably 2.3 moles–3 moles from the economic aspect. In the above-mentioned step viii-2-2, when the amount of acid is less than 2 moles relative to 1 mole of imidazolide (vii), decarbonation reaction may not proceed sufficiently, and the reaction efficiency may decrease. In the above-mentioned step viii-2-2, when the amount of acid to be used exceeds 4 moles relative to 1 mole of imidazolide (vii), the reaction mixture may come to have strong acidity and a side reaction such as racemization, elimination reaction and the like of the resulting product may occur.

This step is carried out generally within a temperature range of −10° C.–40° C., preferably 0° C.–20° C. When the reaction temperature is less than −10° C., the reaction may proceed slowly, or the reaction may not proceed at all, and when the reaction temperature exceeds 40° C., β-ketoester (viii), which is a resulting product, may be decomposed to reduce the reaction yield.

The reaction time of the above-mentioned reaction is not particularly limited and the reaction completes generally in 15 min–30 min.

The solvent to be used for the above-mentioned step viii-2-1 and step viii-2-2 may be any as long as it does not inhibit the reaction and ethers such as THF, dioxane, dimethoxyethane and the like, or a mixed solvent of the ethers with any solvent selected from aromatic hydrocarbons such as benzene, toluene, xylene and the like, aliphatic hydrocarbons such as heptane, hexane, octane and the like can be preferably used. In the case of a mixed solvent, they are mixed at a conventionally known general proportion to make the total amount fall within the above-mentioned range. The solvents to be used for the above-mentioned steps viii-2-1 and viii-2-2 may be the same or different.

The amount of the solvent to be used is generally 1000 mL–5000 mL relative to 1 mole of imidazolide (vii), which is preferably 2000 mL–3000 mL for the smooth progress of the reaction and enhanced productivity.

β-Ketoester (viii) can be isolated and purified by a known isolation method (e.g., extraction, drying and the like) and by a known purification method (e.g., crystallization, silica gel column chromatography method and the like), or may be used as it is in a reaction mixture without isolation and purification.

The malonic acid monoester (v) to be used for the above-mentioned method can be obtained by conventionally known various methods, and commercially available ones can be used.

According to the above-mentioned method, β-ketoester (viii) can be produced efficiently at a lower cost than conventional methods. That is, the above-mentioned method does not use expensive N,N'-carbonyldiimidazole and 1 equivalent amount or 2 equivalent amounts of imidazole compound (iv) is sufficient for reaction, thereby affording production of β-ketoester (viii) efficiently at a lower cost.

The production method of imidazolide (vii) for the above-mentioned method may be esterification, amidation and the like besides synthesis of β-ketoester.

In the above-mentioned production method, by using (R)-3-hydroxy-3-(2-phenylethyl)hexanoic acid [(R)-carboxylic acid (III)] (i.e., a compound of the formula (vi) wherein $R^{1d}$ is 2-hydroxy-2-(2-phenylethyl)pentyl) as carboxylic acid (vi) and setting various same reaction conditions as those for this method, (R)-5-hydroxy-3-oxo-5-(2-phenylethyl)octanoic acid ester [(R)-carboxylic acid ester (X)] can be produced via imidazolide (IX).

The present invention is explained in detail by referring to Examples, which are not to be construed as limitative.

Note that δ in NMR is expressed in ppm.

The optical purity was determined by the following method.

(Optical Purity)

A part of a sample (crystal, etc.) was suspended in toluene and aqueous caustic soda was added. The mixture was stirred for dissolution. The aqueous layer was obtained by partitioning, and made acidic with 10% hydrochloric acid and extracted with toluene. The toluene layer was concentrated and DMF, Hünig's base and benzyl bromide were added. The mixture was heated at 40° C. for 30 min. To the reaction mixture obtained by the above-mentioned heating were added toluene and 10% hydrochloric acid and the aqueous layer was separated by partitioning. The toluene layer was concentrated. The residue was dissolved in isopropanol and both enantiomers [(R) isomer and (S) isomer] were separated by HPLC (solid phase: DAICEL CHIRALCEL OD, mobile phase: 4% isopropanol/hexane). The percentage of the peak area was measured, based on which the optical purity (% e.e.) was determined.

EXAMPLE 1

Racemic Ethyl 3-hydroxy-3-(2-phenylethyl) hexanoate

Magnesium (37.2 g, 1.53 mole) was suspended in THF (60.5 g), and allyl bromide (1.4 g, 0.01 mole) was added in a thin stream. After raising the temperature from 22° C. to 38° C., a solution of dimethyldichlorosilane (7.3 g, 0.06 mole), 1-phenyl-3-hexanone (180.2 g, 1.02 mole), ethyl chloroacetate (139.1 g, 1.13 mole) and allyl bromide (1.4 g, 0.01 mole) in THF (472.9 g) was added at 35–40° C. over 4.7 hr in a thin stream. Further, ethyl chloroacetate (41.7 g, 0.34 mole) was added at 30–40° C. over 1 hr in a thin stream. The mixture was stirred at 40° C. for 1.5 hr and decanted to separate unreacted magnesium. The decanted reaction mixture was added to a mixture of 35% hydrochloric acid (151.8 g, 1.50 mole), ammonium chloride (15.9 g, 0.30 mole) and water (280.7 g) in a thin stream and partitioned at 30–40° C. The organic layer was concentrated to give a residue (342.6 g) containing the title compound (215.1 g, yield 79.6%) (quantitative analysis by HPLC).

$^1$H-NMR (CDCl$_3$, δ ppm) 0.94 (3H, t, J=7.3 Hz), 1.28 (3H, t, J=7 Hz), 1.28–1.41 (2H, m), 1.54–1.59 (2H, m), 1.63–1.83 (2H, m), 2.53–2.69 (2H, m), 3.59 (1H, s), 4.18 (1H, q, J=7 Hz), 4.19 (1H, q, J=7 Hz), 7.18–7.19 (3H, m), 7.27–7.29 (2H, m).

EXAMPLE 2

Racemic Ethyl 3-hydroxy-3-(2-phenylethyl) hexanoate

Magnesium (7.45 g, 0.31 mole) was suspended in THF (12.1 g), and allyl bromide (0.28 g, 0.0023 mole) was added in a thin stream. After raising the temperature from 20° C. to 30° C., a solution of methyltrichlorosilane (3.39 g, 0.0023 mole), 1-phenyl-3-hexanone (40.0 g, 0.227 mole), ethyl chloroacetate (27.81 g, 0.23 mole) and allyl bromide (0.275 g, 0.0023 mole) in THF (94.6 g) was added at 35–40° C. over 2 hr in a thin stream. Further, ethyl chloroacetate (8.34 g, 0.07 mole) was added at 30–40° C. over 40 min in a thin stream.

After stirring at 40° C. for 2 hr, the title compound in the reaction mixture was analyzed and a reaction mixture containing the title compound (46.74 g, yield 77.9%) was obtained (quantitative analysis by HPLC). The NMR data were the same as in Example 1.

EXAMPLE 3

Racemic Ethyl 3-hydroxy-3-(2-phenylethyl) hexanoate

Magnesium (7.45 g, 0.31 mole) was suspended in THF (12.1 g), and allyl bromide (0.28 g, 0.0023 mole) was added in a thin stream. After raising the temperature from 20° C.–30° C., a solution of silicon tetrachloride (3.86 g, 0.023 mole), 1-phenyl-3-hexanone (40.0 g, 0.227 mole), ethyl chloroacetate (27.81 g, 0.23 mole) and allyl bromide (0.275 g, 0.0023 mole) in THF (94.6 g) was added at 35–40° C. over 2 hr in a thin stream. Further, ethyl chloroacetate (8.34 g, 0.07 mole) was added at 30–40° C. over 40 min in a thin stream.

After stirring a 40° C. for 2 hr, the title compound in the reaction mixture was analyzed and a reaction mixture containing the title compound (46.76 g, yield 77.9%) was obtained (quantitative determination analysis by HPLC). The NMR data were the same as in Example 1.

EXAMPLE 4

Racemic Ethyl 3-hydroxy-3-(2-phenylethyl) hexanoate

Magnesium (9.1 g, 0.374 mole) was suspended in THF (99 mL) containing dibenzofuran (1.4109 g) as an internal standard substance and allyl bromide (0.28 g) was added at 31° C. in a thin stream. Thereto was added 2.5 mL of a mixed solution (143 mL) of dimethyldichlorosilane (1.84 g, 14.2 mmole), 1-phenyl-3-hexanone (47.1 g, 0.267 mole), ethyl chloroacetate (34.8 g, 0.284 mole), allyl bromide (0.28 g, 2.3 mmole) and THF (49 mL) at 30° C. in a thin stream. After 18 min, exothermic heat was observed and the internal temperature rose to 32.5° C. After 34 min from the addition in a thin stream, the remaining mixed solution was added at an internal temperature of 32–36° C. over 3 hr in a thin stream. Thereafter, ethyl chloroacetate (10.2 g, 83.2 mmole) was added at an internal temperature of 32–35° C. over 1 hr in a thin stream and thermally insulated at an internal temperature of 36° C. for 1 hr. The title compound in the reaction mixture was analyzed and a reaction mixture containing the title compound (52.5 g, yield 74.3%) was obtained (quantitative analysis by HPLC). The NMR data were the same as in Example 1.

EXAMPLE 5

Racemic ethyl 3-hydroxy-3-(2-phenylethyl) hexanoate

Magnesium (5 g, 0.21 mole) was suspended in THF (17 mL), and allyl bromide (0.35 g, 0.0025 mole) was added for activation. Thereto was added a solution of 1-phenyl-3-hexanone (0.91 g, 5.2 mmole), ethyl chloroacetate (0.63 g, 5.1 mmole) and allyl bromide (6.2 mg, 0.04 mmole) in THF (2.4 mL) in a thin stream.

After stirring for 15 min, the temperature rise was measured. In addition, the yield of the title compound and the residual amount of 1-phenyl-3-hexanone was measured (quantitative analysis by HPLC).

EXAMPLES 6–10

Racemic Ethyl 3-hydroxy-3-(2-phenylethyl) hexanoate

The same procedures as in Example 5 were conducted except that chlorosilane was simultaneously added in a thin stream. The chlorosilanes and the amounts added thereof are as shown in Table 1. The results of Examples 5–10 are as shown in Table 1.

TABLE 1

|  | chlorosilanes | amount added (relative to mole % 1-phenyl-3-hexanone) | Temperature rise (Δ; ° C.) | yield (%) of racemic 3-hydroxy-3-(2-phenyl-ethyl)-hexanoic acid | Residual amount (%) of 1-phenyl-3-hexanone |
| --- | --- | --- | --- | --- | --- |
| Example 5 | none | 0 | 12.5 | 24.6 | 64 |
| Example 6 | Trimethyl-chlorosilane | 10 | 19 | Not measured | Not measured |
| Example 7 | Dimethyl-dichlorosilane | 10 | 19 | 57.9 | 28.6 |
| Example 8 | Dimethyl-dichlorosilane | 5 | 21 | 63.8 | 24.9 |
| Example 9 | Methyl-trichlorosilane | 5 | 24 | 56.6 | 26.3 |
| Example 10 | silicon tetrachloride | 5 | 23.5 | 56.2 | 26.4 |

EXAMPLE 11-1

Ethyl 3-hydroxy-3-(2-phenylethyl)hexanoate

Magnesium (6.8 g, 0.280 mole) was suspended in THF (50 mL), and a solution of 1-phenyl-3-hexanone (22.3 g, 0.127 mole), ethyl chloroacetate (26.0 g, 0.212 mole), zinc chloride (1.93 g, 0.014 mole) and chlorotrimethylsilane (1.54 g, 0.014 mole) in THF (25 mL) was added at 25° C.–30° C. over 2 hr in a thin stream. Further, after stirring at 25° C. for 2.5 hr, 10% hydrochloric acid (70 mL) was added for partitioning to give a THF solution containing the ethyl 3-hydroxy-3-(2-phenylethyl)hexanoate (26.2 g, 78.1%; quantified by absolute calibration curve method (external standard method) using HPLC).

$^1$H-NMR (CDCl$_3$) δ=0.94 (3H, t, J=7.3 Hz), 1.28 (3H, t, J=7 Hz), 1.28–1.41 (2H, m), 1.54–1.59 (2H, m), 1.63–1.83 (2H, m), 2.53–2.69 (2H, m), 3.59 (1H, s), 4.18 (1H, q, J=7 Hz), 4.19 (1H, q, J=7 Hz), 7.18–7.19 (3H, m), 7.27–7.29 (2H, m).

EXAMPLE 11-2

Ethyl 3-hydroxy-3-(2-phenylethyl)hexanoate

Magnesium (5.15 g, 0.212 mole) was suspended in THF (50 mL), and a solution of 1-phenyl-3-hexanone (22.3 g, 0.127 mole), ethyl chloroacetate (26.0 g, 0.212 mole), zinc chloride (1.93 g, 0.014 mole), chlorotrimethylsilane (1.54 g, 0.014 mole) and ethyl acetate (12.2 mL) in THF (25 mL) was added at 25° C.–30° C. over 2 hr in a thin stream. Further, after stirring at 25° C. for 1.5 hr, 10% hydrochloric acid (60 mL) was added for partitioning to give a THF-ethyl acetate solution containing ethyl 3-hydroxy-3-(2-phenylethyl)hexanoate (22.8 g, 68.2%; quantified by absolute calibration curve method (external standard method) using HPLC).

EXAMPLE 11-3

Ethyl 3-hydroxy-3-(2-phenylethyl)hexanoate

Magnesium (5.15 g, 0.212 mole) was suspended in a mixed solvent of THF (25 mL) and toluene (25 mL), and a solution of 1-phenyl-3-hexanone (22.3 g, 0.127 mole), ethyl chloroacetate (26.0 g, 0.212 mole), zinc chloride (1.93 g, 0.014 mole) and chlorotrimethylsilane (1.54 g, 0.014 mole) in THF (25 mL) was added at 25° C.–30° C. over 1.5 hr in a thin stream. Further, after stirring at 25° C. for 2 hr, 10% hydrochloric acid (60 mL) was added for partitioning to give a THF-toluene solution containing the ethyl 3-hydroxy-3-(2-phenylethyl)hexanoate (25.67 g, 76.7%; quantified by absolute calibration curve method (external standard method) using HPLC).

EXAMPLE 11-4 tert-Butyl 3-hydroxy-3-(2-phenylethyl)hexanoate

Magnesium (5.34 g, 0.220 mole) was suspended in THF (50 mL), and 9 mL of a mixture (total amount: 57 mL) of 1-phenyl-3-hexanone (22.33 g, 0.127 mole) and tert-butyl chloroacetate (31.9 g, 0.212 mole), and a solution of zinc chloride (0.48 g, 0.0035 mole) and chlorotrimethylsilane (0.38 g, 0.0035 mole) in THF (5 mL) were added at 25° C.–30° C. over 20 min in a thin stream. Thereafter, the temperature of the reaction mixture was raised to 60° C. and 48 mL of the remaining mixture of the above-mentioned 1-phenyl-3-hexanone and tert-butyl chloroacetate was added at 55° C.–65° C. over 1 hr in a thin stream. Further, after stirring at 60° C. for 1 hr, toluene (50 mL) and 10% hydrochloric acid (60 mL) were added for partitioning to give a THF-toluene solution containing the tert-butyl 3-hydroxy-3-(2-phenylethyl)hexanoate (33.3 g, 89.9%; quantified by absolute calibration curve method (external standard method) using HPLC).

$^1$H-NMR (CDCl$_3$) δ=0.94 (3H, t, J=7.3 Hz), 1.32–1.45 (2H, m), 1.48 (9H, s), 1.51–1.58 (2H, m), 1.77–1.82 (2H, m), 2.44 (2H, s), 2.62–2.70 (2H, m), 3.79 (1H, s), 7.16–7.20 (3H, m), 7.26–7.30 (2H, m).

EXAMPLE 11-5

Ethyl 3-hydroxy-3-(2-phenylethyl)hexanoate

Magnesium (1.98 g, 0.081 mole) was suspended in a mixed solvent of THF (13 mL) and toluene (15 mL), and thereto was added chlorotrimethylsilane (0.2 mL, 0.0016 mole) at 28.5° C. To this suspension was added a mixture of 1-phenyl-3-hexanone (8.93 g, 0.0507 mole) and ethyl chloroacetate (9.94 g, 0.081 mole) at 25° C.–30° C. over 30 min in a thin stream. Further, after stirring at 30° C. for 1.5 hr, 10% hydrochloric acid (30 mL) was added for partitioning to give a THF-toluene solution containing the ethyl 3-hydroxy-3-(2-phenylethyl)hexanoate (9.26 g, 69%; quantified by absolute calibration curve method (external standard method) using HPLC).

EXAMPLE 11-6

Ethyl 3-hydroxy-3-(2-phenylethyl)hexanoate

Magnesium (6.8 g, 0.280 mole) was suspended in THF (25 mL), and thereto was added a mixture of 1-phenyl-3- hexanone (20.09 g, 0.114 mole), ethyl chloroacetate (20.8 g, 0.170 mole) and chlorotrimethylsilane (15.4 g, 0.142 mole) at 25° C. over 90 min in a thin stream. The mixture was stirred at 25° C. for 2 hr and treated with diluted hydrochloric acid to give a THF solution containing ethyl 3-hydroxy-3-(2-phenylethyl)hexanoate (15.54 g, 51.6%; quantified by the absolute calibration curve method (external standard method) using HPLC).

EXAMPLE 11-7

Ethyl 3-hydroxy-3-(2-phenylethyl)hexanoate

Magnesium (13.6 g, 0.559 mole) was suspended in THF (50 mL), and thereto was added a mixture of 1-phenyl-3-hexanone (20.09 g, 0.114 mole), ethyl chloroacetate (34.8 g, 0.284 mole) and chlorotrimethylsilane (15.4 g, 0.142 mole) at 20° C.–30° C. over 180 min in a thin stream. The mixture was stirred at 20° C.–30° C. for 2 hr and treated with diluted hydrochloric acid to give a THF solution containing ethyl 3-hydroxy-3-(2-phenylethyl)hexanoate (21.8 g, yield: 72.3%; quantified by absolute calibration curve method (external standard method) using HPLC).

EXAMPLE 11-8

Ethyl 3-hydroxy-3-(2-phenylethyl)hexanoate

Magnesium (13.6 g, 0.559 mole) was suspended in THF (50 mL), and thereto was added a mixture of 1-phenyl-3-hexanone (20.09 g, 0.114 mole), ethyl chloroacetate (34.8 g, 0.284 mole) and chlorotrimethylsilane (15.4 g, 0.142 mole) at 60° C. over 180 min in a thin stream. The mixture was stirred at 60° C. for 2 hr and treated with diluted hydrochloric acid to give a THF solution containing ethyl 3-hydroxy-3-(2-phenylethyl)hexanoate (18.64 g, 61.8%; quantified by absolute calibration curve method (external standard method) using HPLC).

EXAMPLE 11-9

Ethyl 3-hydroxy-3-(2-phenylethyl)hexanoate

Magnesium (1.73 g, 71.2 mmole) was suspended in THF (15 mL), and iodine (20 mg) was added thereto. To the suspension was added 1 mL from a mixture (total amount: 18 mL) of 1-phenyl-3-hexanone (8.93 g, 50.7 mmole) and ethyl chloroacetate (8.70 g, 70.99 mmole) at 30° C. in a thin stream. The mixture was stirred for 15 min and the remaining (17 mL) of the above-mentioned mixture (total amount: 18 mL) of 1-phenyl-3-hexanone and ethyl chloroacetate was added at 30° C.–40° C. over 2 hr in a thin stream. The mixture was stirred at 30° C. for 2 hr and 10% hydrochloric acid (20 mL) was added for partitioning, which gave a THF solution containing ethyl 3-hydroxy-3-(2-phenylethyl) hexanoate (10.2 g, 75.2%; quantified by absolute calibration curve method (external standard method) using HPLC).

EXAMPLE 11-10

Ethyl 3-hydroxy-3-(2-phenylethyl)hexanoate

Magnesium (1.98 g, 81.4 mmole) was suspended in THF (15 mL), and iodine (10 mg) was added thereto. To the suspension was added 1 mL from a mixture (total amount: 20 mL) of 1-phenyl-3-hexanone (8.93 g, 50.7 mmole) and ethyl chloroacetate (9.94 g, 81.1 mmole) at 25° C. in a thin stream. The mixture was stirred for 10 min and allowed to warm the internal temperature to 30° C. The remaining (19 mL) of the above-mentioned mixture (total amount: 20 mL) of 1-phenyl-3-hexanone and ethyl chloroacetate was added at 30° C.–40° C. over 2 hr in a thin stream. The mixture was stirred at 30° C. for 1 hr, and 10% hydrochloric acid (30 mL) was added for partitioning, which gave a THF solution containing ethyl 3-hydroxy-3-(2-phenylethyl)hexanoate (10.2 g, 76%; quantified by absolute calibration curve method (external standard method) using HPLC).

EXAMPLE 11-11

Ethyl 3-hydroxy-3-(2-phenylethyl)hexanoate

Magnesium (2.20 g, 90.5 mmole) was suspended in THF (15 mL), and iodine (10 mg) was added thereto. To the suspension was added 1 mL from a mixture of (total amount: 21 mL) of 1-phenyl-3-hexanone (8.93 g, 50.7 mmole) and ethyl chloroacetate (11.19 g, 91.3 mmole) at 25° C. in a thin stream. The mixture was stirred for 10 min and allowed to warm the internal temperature to 35° C. The remaining (20 mL) of the above-mentioned mixture (total amount: 21 mL) of 1-phenyl-3-hexanone and ethyl chloroacetate was added at 30° C.–40° C. over 2 hr in a thin stream. The mixture was stirred at 30° C. for 1 hr and 10% hydrochloric acid (30 mL) was added for partitioning, which gave a THF solution containing ethyl 3-hydroxy-3-(2-phenylethyl)hexanoate (9.42 g, 70.5%; quantified by absolute calibration curve method (external standard method) using HPLC).

EXAMPLE 11-12

Ethyl 3-hydroxy-3-(2-phenylethyl)hexanoate

Magnesium (1.98 g, 81.4 mmole) was suspended in THF (15 mL), and iodine (10 mg) was added thereto. The suspension was allowed to warm 50° C. A mixture (total amount: 20 mL) of 1-phenyl-3-hexanone (8.93 g, 50.7 mmole) and ethyl chloroacetate (9.94 g, 81.1 mmole) added at 50° C.–55° C. over 2 hr in a thin stream. The reaction mixture was stirred at 55° C. for 1 hr and 10% hydrochloric acid (30 mL) was added for partitioning, which gave a THF solution containing ethyl 3-hydroxy-3-(2-phenylethyl) hexanoate (8.88 g, 66%; quantified by absolute calibration curve method (external standard method) using HPLC).

EXAMPLE 11-13

Ethyl 3-hydroxy-3-(2-phenylethyl)hexanoate

Magnesium (1.98 g, 81.4 mmole) was suspended in a mixed solvent of THF (7.5 mL) and heptane (7.5 mL), and iodine (10 mg) was added thereto. The suspension was allowed to warm to 50° C. A mixture (total amount: 20 mL) of 1-phenyl-3-hexanone (8.93 g, 50.7 mmole) and ethyl chloroacetate (9.94 g, 81.1 mmole) was added at 50° C.–60° C. over 2 hr in a thin stream. The mixture was stirred at 55° C. for 1 hr and 10% hydrochloric acid (30 mL) was added for partitioning, which gave a THF solution containing ethyl 3-hydroxy-3-(2-phenylethyl)hexanoate (8.58 g, 63.8%; quantified by absolute calibration curve method (external standard method) using HPLC).

EXAMPLE 11-14

Isopropyl 3-hydroxy-3-(2-phenylethyl)hexanoate

Magnesium (2.77 g, 113.9 mmole) was suspended in THF (15 mL), and iodine (10 mg) was added thereto. To the suspension was added 1.5 mL from a mixture (total amount: 31 mL) of 1-phenyl-3-hexanone (13.4 g, 76.0 mmole) and isopropyl chloroacetate (15.58 g, 114.1 mmole) at 24° C. in a thin stream, and the mixture was stirred at 23° C.–27° C. for 30 min. The reaction mixture was allowed to warm to 45° C. The remaining (29.5 mL) of the above-mentioned mixture (total amount: 31 mL) of 1-phenyl-3-hexanone and isopropyl chloroacetate added at 40° C.–50° C. over 2 hr in a thin stream. The mixture was stirred at 66° C. for 1.5 hr and 10% hydrochloric acid (30 mL) was added for partitioning, which gave a THF solution containing isopropyl 3-hydroxy-3-(2-phenylethyl)hexanoate (15.7 g, 74%; quantified by absolute calibration curve method (external standard method) using HPLC).

$^1$H-NMR (CDCl$_3$) δ=0.94 (3H, t, J=7.3 Hz), 1.25 (3H, d, J=6 Hz), 1.26 (3H, d, J=6 Hz), 1.35–1.43 (2H, m), 1.53–1.59 (2H, m), 1.78–1.82 (2H, m), 2.50 (2H, s), 2.64–2.69 (2H, m), 3.66 (1H, s), 5.08 (1H, sept, J=6 Hz), 7.16–7.19 (3H, m), 7.26–7.29 (2H, m).

EXAMPLE 11-15

Ethyl 3-hydroxy-3-(2-phenylethyl)hexanoate

Magnesium (1.48 g, 60.9 mmole) was suspended in THF (10 mL), and thereto was added 2 mL from a mixture (total amount: 17 mL) of 1-phenyl-3-hexanone (8.93 g, 50.7 mmole) and ethyl chloroacetate (7.46 g, 60.9 mmole) at 30° C. in a thin stream. A heat development was observed when stirring the mixture and, after 15 min, the temperature was reached 40° C. The mixture was cooled to have the internal temperature of 33° C., and the remaining (15 mL) of the above-mentioned mixture (total amount: 17 mL) of 1-phenyl-3-hexanone and ethyl chloroacetate added at 30° C.–35° C. over 2 hr in a thin stream. The mixture was stirred at 30° C. for 2.5 hr and toluene (20 mL) was added thereafter. 10% Hydrochloric acid (20 mL) was added for partitioning to give a THF-toluene solution containing ethyl 3-hydroxy-3-(2-phenylethyl)hexanoate (8.33 g, 62.2%; quantified by absolute calibration curve method (external standard method) using HPLC).

EXAMPLE 11-16 tert-Butyl 3-hydroxy-3-(2-phenylethyl)hexanoate

Magnesium (1.18 g, 48.6 mmole) was suspended in THF (8 mL), and iodine (5 mg) was added thereto. A solution of ethyl bromoacetate (35 mg, 0.2 mmole) in THF (0.2 mL) was then added in a thin stream. To the suspension was added 1 mL from a mixture (total amount: 16 mL) of 1-phenyl-3-hexanone (7.14 g, 40.5 mmole) and tert-butyl chloroacetate (7.34 g, 48.7 mmole) at 34° C. in a thin stream and the mixture was allowed to warm to 55° C. At the temperature, the mixture was stirred for 10 min and the remaining (15 mL) of the above-mentioned mixture (total amount: 16 mL) of 1-phenyl-3-hexanone and tert-butyl chloroacetate was added at 55° C.–65° C. over 1.5 hr in a thin stream. The mixture was stirred at 66° C. for 1 hr, and toluene (10 mL) and 10% hydrochloric acid (10 mL) were added for partitioning to give a THF-toluene solution containing tert-butyl 3-hydroxy-3-(2-phenylethyl)hexanoate (7.47 g, 63.1%; quantified by absolute calibration curve method (external standard method) using HPLC).

EXAMPLE 12

1-phenyl-3-hexanone (1) Propyl Styryl Ketone (3-oxo-1-phenyl-1-hexene)

To a mixture of benzaldehyde (30.00 g, 0.283 mole) and 2-pentanone (67.33 g, 0.782 mole) was added 10% aqueous sodium hydroxide (40.00 g, 0.10 mole) and the mixture was heated and stirred at 55–65° C. for 10 hr. The reaction mixture was cooled to room temperature and the aqueous layer was once separated. 5% Brine (20 g) was added and after stirring, the aqueous layer was separated. This step was repeated twice. The low boiling point content such as 2-pentanone, benzaldehyde and the like in the obtained organic layer were distilled away under reduced pressure to give the title compound as a pale-yellow green oil (138–150° C./1.33 kPa). (39.25 g, yield 79.7%)

$^1$H-NMR (CDCl$_3$) δ: 0.99 (t, 3H, J=7.3 Hz, CH$_3$), 1.65–1.80 (m, 2H, CH$_2$), 2.65 (t, 2H, J=7.3 Hz, CH$_2$CO), 6.72 (s, 1H, olefinic), 6.77 (s, 1H, olefinic), 7.3–7.6 (m, 5H, aromatic).

(2) 1-phenyl-3-hexanone

To a solution of propyl styryl ketone (20.00 g, 0.115 mole) obtained above in ethyl acetate (70 ml) was added 5% Pd—C (0.8 g, BNA-Type, manufactured by N.E. CHEMCAT CORPORATION) and reduction reaction was conducted at room temperature for 2 hr under 1 atm hydrogen pressure. The catalyst was filtered off and the filtrate was washed with ethyl acetate. Ethyl acetate in the obtained filtrate was distilled away to give the title compound as a colorless oil (20.11 g, yield 99.4%). $^1$H-NMR (CDCl$_3$) δ: 0.89 (t, 3H, J=7.6 Hz, CH$_3$), 1.50–1.70 (m, 2H, CH$_2$), 2.36 (t, 2H, J=7.4 Hz, CH$_2$CO), 2.72 (t, 2H, J=8.0 Hz, CH$_2$), 2.90 (t, 2H, J=8.0 Hz, CH$_2$), 7.05–7.35 (m, 5H, aromatic).

EXAMPLE 13

Racemic 3-hydroxy-3-(2-phenylethyl)hexanoic acid

To the residue (342.6 g, including 215.1 g of racemic ethyl 3-hydroxy-3-(2-phenylethyl)hexanoate) obtained in Example 1 was added 10% aqueous sodium hydroxide (590 g, 1.48 mole) and the mixture was stirred at 40–50° C. for 4 hr. To the reaction mixture were added 19% hydrochloric acid (216.4 g, 1.11 mole) and MIBK (150.4 g), and, after stirring, partitioned to give an organic layer (455.7 g) containing the title compound (189.8 g, yield 98.7%) (Quantitative analysis by HPLC).

$^1$H-NMR (CDCl$_3$, δ ppm) 0.96 (3H, t, J=7 Hz), 1.35–1.47 (2H, m), 1.60–1.64 (2H, m), 1.84–1.89 (2H, m), 2.60 (2H, s), 2.65–2.70 (2H, m), 7.17–7.20 (3H, m), 7.26–7.30 (2H, m).

EXAMPLE 14

(R)-N-(3,4-dimethoxybenzyl)-1-phenylethylamine

Veratraldehyde (174.5 g, 1.05 mole) was dissolved in isopropanol (600 ml) at 10–40° C. and (R)-1-phenylethylamine (121.2 g, 1.00 mmole) was added at 50–60° C. over 1–2 hr in a thin stream. Further, after stirring at 50–60° C. for 1–2 hr, the mixture was cooled to 20° C. To this solution were added triethylamine (5.1 g, 50.0 mmole) and 5% palladium carbon (50% wet, 5.4 g) at 20–30° C. and the mixture was stirred under 1 atm hydrogen atmosphere at 40–45° C. for 7–8 hr. The catalyst was filtered off and the filtrate was concentrated to give the title compound (277.5 g, pure amount 252.5 g, yield 93.05%) (Quantitative analysis by HPLC).

IR (ν cm$^{-1}$) 3325 (N—H), 1514 (N—H).

REFERENCE EXAMPLE 1

(R)-N-(3,4-dimethoxybenzyl)-α-phenylethylamine 3,4-Dimethoxybenzaldehyde (67.51 g, 0.406 mole) was dissolved in methanol (240 mL) and R-1-phenylethylamine (48.47 g, 0.4 mole) was added at 50° C. in a thin stream. The mixture was stirred at the same temperature for 1 hr. Sodium borohydride (9.08 g) was added at 20° C.–30° C. and the mixture was stirred overnight. The mixture was extracted with toluene, washed and concentrated to give (R)-N-(3,4-dimethoxybenzyl)-α-phenylethylamine (107.1 g). The yield was 98.67%.

IR spectrum: (ν cm$^{-1}$) 3325 (N—H), 1514 (N—H)

REFERENCE EXAMPLE 2

(R)-N-(o-chlorobenzyl)-α-phenylethylamine

In the same manner as in Reference Example 1 except that 2-chlorobenzaldehyde was used instead of 3,4-dimethoxybenzaldehyde, (R)-N-(o-chlorobenzyl)-α-phenylethylamine was obtained. The yield was 98.5%.

IR spectrum: (ν cm$^{-1}$) 3322 (N—H), 1444 (N—H)

EXAMPLE 15

(R)-3-hydroxy-3-(2-phenylethyl)hexanoic Acid.(R)-N-(3,4-dimethoxybenzyl)-1-phenylethylamine Salt To a solution (445.7 g, pure content of racemic 3-hydroxy-3-(2-phenylethyl)hexanoic acid 189.8 g, 0.803 mole) of racemic 3-hydroxy-3-(2-phenylethyl)hexanoic acid obtained in Example 13 in MIBK was added MIBK (1420 mL). The mixture was heated to 55–60° C. and a solution (300 mL) of (R)-N-(3,4-dimethoxybenzyl)-1-phenylethylamine (215.6 g, pure content 196.16 g, 0.723 mole) in MIBK was added over 15 min in a thin stream. When cooled to 51° C. over 30 min, a crystal of (R)-3-hydroxy-3-(2-phenylethyl)hexanoic acid.(R)-N-(3,4-dimethoxybenzyl)-1-phenylethylamine salt was inoculated and, after cooling to 45–49° C., the mixture was stirred at the same temperature for 30 min. After cooling to 25° C. over 2 hr, the mixture was stirred at the same temperature for 2 hr. The resulting crystal was collected by filtration and washed with MIBK (320 mL) to give a crude crystal of the title salt as a colorless crystal (181.26 g, yield 44.45%, optical purity 92.6% e.e.).

EXAMPLE 16

Purification of (R)-3-hydroxy-3-(2-phenylethyl) hexanoic Acid.(R)-N-(3,4-dimethoxybenzyl)-1-phenylethylamine Salt A crude crystal (238.46 g, optical purity 92.0% e.e.) of (R)-3-hydroxy-3-(2-phenylethyl)hexanoic acid.(R)-N-(3,4-dimethoxybenzyl)-1-phenylethylamine salt obtained in the same manner as in Example 15 was dissolved in MIBK (2385 mL) at 80° C. The mixture was cooled to 76° C. and (R)-3-hydroxy-3-(2-phenylethyl)hexanoic acid.(R)-N-(3,4-dimethoxybenzyl)-1-phenylethylamine salt was inoculated. The mixture was stirred at 63–67° C. for 1 hr. After cooling to 25° C. over 10 hr, the resulting crystal was collected by filtration and washed with MIBK (250 mL) to give the title salt as a colorless crystal (216.37 g, yield 90.74%, optical purity 99.55% e.e.).

EXAMPLE 17

(R)-3-hydroxy-3-(2-phenylethyl)hexanoic Acid.(R)-N-(3,4-dimethoxybenzyl)-1-phenylethylamine Salt To a solution (468.5 g, pure content of racemic 3-hydroxy-3-(2-phenylethyl)hexanoic acid 202.6 g, 0.857 mole) of racemic 3-hydroxy-3-(2-phenylethyl)hexanoic acid obtained in the same manner as in Example 13 in MIBK was added a filtrate (1536 mL, including (R)-3-hydroxy-3-(2-phenylethyl)hexanoic acid.(R)-N-(3,4-dimethoxybenzyl)-1-phenylethylamine salt 0.026 mole) obtained in Example 16. The mixture was heated to 60–63° C. Thereto was added a solution of (R)-N-(3,4-dimethoxybenzyl)-1-phenylethylamine (229.3 g, pure content 209.4 g, 0.7716 mole) dissolved in the filtrate obtained Example 16 (300 mL, containing (R)-3-hydroxy-3-(2-phenylethyl)hexanoic acid. (R)-N-(3,4-dimethoxybenzyl)-1-phenylethylamine salt 0.005 mole) over 15 min in a thin stream. After cooling to 58° C. over 30 min, a crystal of (R)-3-hydroxy-3-(2-phenylethyl)hexanoic acid.(R)-N-(3,4-dimethoxybenzyl)-1-phenylethylamine salt was inoculated and the mixture was stirred at 50° C. for 30 min. After cooling to 25° C. over 12 hr, the mixture was filtrated and washed with MIBK (340 mL) to give a crude crystal of the title salt as a colorless crystal (207.5 g, 47.68%, 94.6% e.e.).

EXAMPLE 18

(R)-3-hydroxy-3-(2-phenylethyl)hexanoic Acid (R)-3-Hydroxy-3-(2-phenylethyl)hexanoic acid.(R)-N-(3,4-dimethoxybenzyl)-1-phenylethylamine salt (180.58 g, 355.7 mmole) was suspended in MIBK (542 mL), and thereto was added 10% sulfuric acid (355.6 g) and the mixture was stirred for 30 min. After the aqueous layer (aqueous layer 1) was removed by partitioning and water (50 g) was added to the organic layer. After stirring for 30 min, the aqueous layer was removed (aqueous layer 2).

To the organic layer was added dilute aqueous sulfuric acid (50 g, pH 2) and the mixture was stirred, washed and partitioned to remove the aqueous layer. The organic layer was again washed with dilute aqueous sulfuric acid (50 g, pH 2). To the organic layer was added 0.04% aqueous sodium hydroxide (50 g) and the mixture was stirred and the aqueous layer was removed by partitioning. The organic layer was concentrated (6.4 KPa, internal temperature to 87° C.) to give the title compound as a colorless oil (91.5 g, purity 87.9%, pure amount 80.43 g) (Quantitative analysis by HPLC). NMR data were the same as in Example 13.

EXAMPLE 19

Recovery of (R)-N-(3,4-dimethoxybenzyl)-1-phenylethylamine

The filtrates (containing solvent MIBK, 1964.8 g, 3-hydroxy-3-(2-phenylethyl)hexanoic acid 0.4313 mole, (R)-N-(3,4-dimethoxybenzyl)-1-phenylethylamine 95.98 g, 0.3537 mole) obtained in Example 15 and 17 were extracted once with 10% sulfuric acid (431.1 g) and once with 10% sulfuric acid (215 g). The aqueous layers were combined (764.5 g), MIBK (485 g) was added, and 20% aqueous sodium hydroxide (277.2 g) was added. The mixture was stirred and stood still. The aqueous layer was removed and water (291 g) was added to the organic layer. The mixture was again stirred and stood still. The aqueous layer was removed and the organic layer was concentrated to give the title compound as a colorless oil (105.87 g, purity 87.33%, pure amount 92.46 g, yield 96.3%) (Quantitative determination analysis by HPLC).

EXAMPLE 20

Recovery of (R)-N-(3,4-dimethoxybenzyl)-1-phenylethylamine

To a mixture of aqueous layer 1 and aqueous layer 2 (642.7 g, including (R)-N-(3,4-dimethoxybenzyl)-1- phenylethylamine 96.5 g) obtained in Example 18 was added MIBK (386 g) and 20% aqueous sodium hydroxide (149.4 g) was added. The mixture was stirred and stood still. The aqueous layer was removed and water (290 g) was added to the organic layer. The mixture was again stirred and stood still. The aqueous layer was removed to give an MIBK solution containing the title compound (417.4 g, purity 21.86%, pure amount 91.26 g, yield 94.55%) (Quantitative determination analysis by HPLC).

EXAMPLE 21-1

(R)-3-hydroxy-3-(2-phenylethyl)hexanoic acid (R)-N-(3,4-dimethoxybenzyl)-α-phenylethylamine Salt To a solution of racemic 3-hydroxy-3-(2-phenylethyl) hexanoic acid (21.3 g, purity: 83.2%, pure amount: 17.72 g, 75 mmole) in MIBK (270 mL) was added (R)-N-(3,4-dimethoxybenzyl)-α-phenylethylamine (18.32 g, 67.5 mmole) and dissolved at 60° C. After cooling to 55° C., (R)-N-(3,4-dimethoxybenzyl)-α-phenylethylamine salt (20 mg) of (R)-3-hydroxy-3-(2-phenylethyl)hexanoic acid was added. Thereafter, The mixture was cooled to 30° C. and stirred at the same temperature for 2 hr. The resulting crystal was collected by filtration to give an amine salt (15.50 g, yield: 40.7%) of (R)-3-hydroxy-3-(2-phenylethyl)hexanoic acid having an optical purity of 90% e.e.

EXAMPLE 21-2

Purification of (R)-3-hydroxy-3-(2-phenylethyl) hexanoic Acid.(R)-N-(3,4-dimethoxybenzyl)-α-phenylethylamine Salt The (R)-N-(3,4-dimethoxybenzyl)-α-phenylethylamine salt (15.0 g) of (R)-3-hydroxy-3-(2-phenylethyl)hexanoic acid obtained in Example 21-1 and having an optical purity of 90% e.e. was dissolved in MIBK (180 mL) at 75° C. After cooling the obtained solution to 65° C., (R)-N-(3,4-dimethoxybenzyl)-α-phenylethylamine salt (20 mg) of (R)-3-hydroxy-3-(2-phenylethyl)hexanoic acid was added and the solution was cooled to 30° C. The resulting salt was collected by filtration to give an amine salt (13.2 g, yield: 86.8%) of (R)-3-hydroxy-3-(2-phenylethyl)hexanoic acid with 99.4% e.e. (the total yield: 35.3%).

EXAMPLE 21-3

(R)-3-hydroxy-3-(2-phenylethyl)hexanoic Acid.(R)-N-(o-chlorobenzyl)-α-phenylethylamine Salt To a solution of racemic 3-hydroxy-3-(2-phenylethyl) hexanoic acid (7.34 g, purity: 80.5%, pure amount: 5.91 g, 25 mmole) in MIBK (90 mL) was added (R)-N-(o-chlorobenzyl)-α-phenylethylamine (5.53 g, 22.5 mmole), and dissolved at 55° C. After cooling to 50° C., (R)-N-(o-chlorobenzyl)-α-phenylethylamine salt (20 mg) of (R)-3-hydroxy-3-(2-phenylethyl)hexanoic acid was added. Thereafter, the mixture was cooled to 30° C. and stirred at the same temperature for 2 hr. The resulting salt was collected by filtration to give an amine salt (5.30 g, yield: 44.0%) of (R)-3-hydroxy-3-(2-phenylethyl)hexanoic acid having an optical purity of 84% e.e.

EXAMPLE 21-4

Purification of (R)-3-hydroxy-3-(2-phenylethyl) hexanoic Acid.(R)-N-(o-chlorobenzyl)-α-phenylethylamine Salt The (R)-N-(o-chlorobenzyl)-α-phenylethylamine salt (5.0 g) of (R)-3-hydroxy-3-(2-phenylethyl)hexanoic acid obtained in Example 21-3 and having an optical purity of 84% e.e. is dissolved in MIBK (75 mL) at 75° C. After cooling to 60° C., (R)-N-(o-chlorobenzyl)-α-phenylethylamine salt (20 mg) of (R)-3-hydroxy-3-(2-phenylethyl)hexanoic acid was added. The mixture was cooled to 25° C. and the resulting salt was collected by filtration to give an amine salt (4.1 g, yield: 82%) of (R)-3-hydroxy-3-(2-phenylethyl)hexanoic acid having an optical purity of 97.6% e.e. (the total yield: 36.1%).

EXAMPLE 21-5

(R)-3-hydroxy-3-(2-phenylethyl)hexanoic Acid.(R)-N-(o-chlorobenzyl)-α-phenylethylamine Salt To an ethyl acetate (90 mL) solution of racemic 3-hydroxy-3-(2-phenylethyl)hexanoic acid (7.34 g, purity: 80.5%, pure amount: 5.91 g, 25 mmole) was added (R)-N-(o-chlorobenzyl)-α-phenylethylamine (5.53 g, 22.5 mmole) at 60° C. in a thin stream. After adding (R)-N-(o-chlorobenzyl)-α-phenylethylamine salt (20 mg) of (R)-3-hydroxy-3-(2-phenylethyl)hexanoic acid, the mixture was allowed to cool to 30° C. and stirred at the same temperature for 2 hr. The resulting salt was collected by filtration to give an amine salt (4.46 g, yield: 37.0%) of (R)-3-hydroxy-3-(2-phenylethyl)hexanoic acid having an optical purity of 86% e.e.

EXAMPLE 21-6

(R)-3-hydroxy-3-(2-phenylethyl)hexanoic Acid.(R)-N-(3,4-dimethoxybenzyl)-α-phenylethylamine Salt To an ethyl acetate (90 mL) solution of racemic 3-hydroxy-3-(2-phenylethyl)hexanoic acid (7.34 g, purity: 80.5%, pure amount: 5.91 g, 25 mmole) was added (R)-N-(3,4-dimethoxybenzyl)-α-phenylethylamine (6.11 g, 22.5 mmole) and dissolved at 60° C. After cooling to 50° C., (R)-N-(3,4-dimethoxybenzyl)-α-phenylethylamine salt (20 mg) of (R)-3-hydroxy-3-(2-phenylethyl)hexanoic acid was added. The mixture was allowed to cool to 30° C. and stirred at the same temperature for 2 hr. The resulting salt was collected by filtration to give an amine salt (5.17 g, yield: 40.9%) of (R)-3-hydroxy-3-(2-phenylethyl)hexanoic acid having an optical purity of 87% e.e.

EXAMPLE 21-7

Purification of (R)-3-hydroxy-3-(2-phenylethyl) hexanoic Acid.(R)-N-(3,4-dimethoxybenzyl)-α-phenylethylamine Salt The (R)-N-(3,4-dimethoxybenzyl)-α-phenylethylamine salt (5.0 g) of (R)-3-hydroxy-3-(2-phenylethyl)hexanoic acid obtained in Example 21-6 and having an optical purity of 87% e.e. was recrystallized in the same manner as in Example 21-4 to give amine salt (4.23 g, yield: 84.5%, the total yield: 34.6%) of (R)-3-hydroxy-3-(2-phenylethyl) hexanoic acid having an optical purity of 99.2% e.e.

REFERENCE EXAMPLE 3

(R)-3-hydroxy-1-(1-imidazolyl)-3-(2-phenylethyl)hexane-1-one (R)-3-Hydroxy-3-(2-phenylethyl)hexanoic acid (1.0 g, 4.2317 mmole), imidazole (0.3457 g, 5.078 mmole) and triethylamine (0.9206 g, 9.098 mmole) were dissolved in THF (6 mL) and cooled to −20° C.–0° C. To this solution was gradually added thionyl chloride (0.559 g, 4.2317 mmole) diluted in THF (4 mL) while maintaining at −20° C.–0° C. in a thin stream. After completion of addition in a thin stream, the mixture was stirred while maintaining at −20° C.–0° C. for 30 min to give a THF solution containing (R)-3-hydroxy-1-(1-imidazolyl)-3-(2-phenylethyl)hexane-1-one (yield not less than 90%, treated with n-butylamine, stirred at 20–30° C. for 30 min–1 hr, converted to an amide form and quantitatively determined as an amide form by absolute calibration method using HPLC).

REFERENCE EXAMPLE 4

Ethyl (R)-5-hydroxy-3-oxo-5-(2-phenylethyl) octanoate

Potassium monoethyl malonate (1.080 g, 6.348 mmole) was added to a suspension of magnesium chloride (0.5437 g, 5.713 mmole) and THF (4 mL) and the mixture was stirred at 40° C. for 2 hr. To this suspension was added the total amount of a solution of (R)-3-hydroxy-1-(1-imidazolyl)-3-(2-phenylethyl)hexane-1-one in THF obtained in Reference Example 3 at 40° C., and the mixture was stirred at 60° C. for 6 hr. After cooling to 0° C., 10% aqueous hydrochloric acid (4.4 g) was gradually added in a thin stream and the mixture was stirred at 0° C. for 15 min. After standing still, the mixture was partitioned and the aqueous layer was removed. Saturated brine (4 g) was added to the organic layer and the mixture was stirred for 15 min while maintaining the temperature. After standing still, the mixture was partitioned and the aqueous layer was removed. Anhydrous magnesium sulfate (1 g) was added to the organic layer and dried. Magnesium sulfate was filtered off and the obtained filtrate was concentrated under reduced pressure to give a crude product (1.45 g) of ethyl (R)-5-hydroxy-3-oxo-5-(2-phenylethyl)octanoate. This was purified by silica gel column chromatography to give ethyl (R)-5-hydroxy-3-oxo-5-(2-phenylethyl)octanoate (0.875 g, yield 67.5%).

$^1$H-NMR (CDCl$_3$) δ=0.92–0.96 (3H, t, J=18 Hz), 1.25–1.37 (5H, m), 1.55–1.60 (2H, m), 1.80–1.85 (2H, m), 2.61–2.68 (2H, m), 2.77 (2H, s), 3.44 (2H, s), 4.16–4.22 (2H, q, J=18 Hz), 7.17–7.30 (5H, m)

REFERENCE EXAMPLE 5

(R)-3-hydroxy-1-(1-imidazolyl)-3-(2-phenylethyl) hexane-1-one

Imidazole (1.819 g, 26.619 mmole) and triethylamine (3.060 g, 30.249 mmole) were dissolved in dry THF (20 mL) and cooled to 0° C. To this solution was gradually added thionyl chloride (1.647 g, 12.463 mmole) in a thin stream and the mixture was stirred for 30 min while maintaining at 0° C. The obtained cloudy solution was gradually added to a solution of (R)-3-hydroxy-3-(2-phenylethyl)hexanoic acid (3.0 g, 12.100 mmole) diluted with dry THF (10 mL) and cooled to −20° C.–−15° C., so that the internal temperature would not exceed −10° C. in a thin stream and further washed with dry THF (5 mL), which was also added in a thin stream. After completion of the addition in a thin stream, the mixture was stirred while maintaining at −20° C. to −15° C. for 1 hr, to give a THF solution containing (R)-3-hydroxy-1-(1-imidazolyl)-3-(2-phenylethyl)hexane-1-one (yield 100%, quantitative analysis in the same manner as in Reference Example 3).

REFERENCE EXAMPLE 6

Ethyl 3-(2,6-dichloro-5-fluoropyridyl)-3-oxo-propionate

In the same manner as in Reference Example 3 and Reference Example 4, ethyl 3-(2,6-dichloro-5-fluoropyridyl)-3-oxo-propionate is obtained from 2,6-dichloro-5-fluoronicotinic acid.

REFERENCE EXAMPLE 7

Ethyl 2-(cinnamoyl)acetate

In the same manner as in Reference Example 3 and Reference Example 4, ethyl 2-(cinnamoyl)acetate is obtained from cinnamic acid.

REFERENCE EXAMPLE 8

Ethyl 2-(4-hydroxyphenylacetyl)acetate

In the same manner as in Reference Example 3 and Reference Example 4, ethyl 2-(4-hydroxyphenylacetyl)acetate is obtained from 4-hydroxybenzoic acid.

INDUSTRIAL APPLICABILITY

According to the present invention, a method for providing (R)-3-hydroxy-3-(2-phenylethyl)hexanoic acid useful as a starting material of a pharmaceutical agent can be efficiently produced from racemic 3-hydroxy-3-(2-phenylethyl)hexanoic acid with a high optical purity and relatively high total yield can be provided.

In addition, the present invention produces 3-hydroxy-3-(2-phenylethyl)hexanoic acid ester safely and at a lower cost than a conventional method.

This application is based on a patent application Nos. 2002-30724, 2002-41480, 2002-105772 and 2002-242741 filed in Japan, the contents of which are hereby incorporated by reference.

What is claimed is:

1. A production method of (R)-3-hydroxy-3-(2-phenylethyl)hexanoic acid, which comprises optically resolving racemic 3-hydroxy-3-(2-phenylethyl)hexanoic acid using an optically active amine of the formula (VIII)

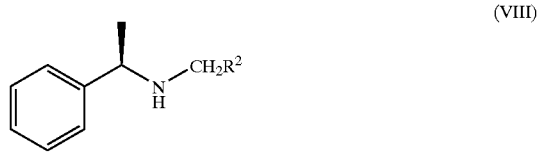

(VIII)

wherein R$^2$ is 3,4-dimethoxyphenyl or 2-chlorophenyl.

2. The production method of claim 1, wherein a salt of (R)-3-hydroxy-3-(2-phenylethyl)hexanoic acid with the optically active amine (VIII) is crystallized in one or more kinds of solvents selected from ethyl acetate, methanol, isopropanol, ethanol, acetonitrile, methyl isobutyl ketone, acetone, methyl ethyl ketone, diisopropyl ether, dimethoxyethane and tetrahydrofuran, wherein the solvent optionally further contains water.

3. The production method of claim 1, wherein the optically active amine (VIII) is obtained by condensing (R)-1-phenylethylamine with a compound of the formula R$^2$—CHO (VIII-i) wherein R$^2$ is as defined above, and reducing the resulting compound.

4. The production method of claim 1, which comprises recovering the optically active amine (VIII) after optical resolution.

5. A production method of (R)-3-hydroxy-3-(2-phenylethyl)hexanoic acid, which comprises hydrolyzing a racemic 3-hydroxy-3-(2-phenylethyl)hexanoic acid ester to produce racemic 3-hydroxy-3-(2-phenylethyl)hexanoic acid, extracting the compound with one or more kinds of solvents selected from ethyl acetate, methyl isobutyl ketone, methyl ethyl ketone, diisopropyl ether and tetrahydrofuran, and optically resolving the compound by crystallizing a salt of (R)-3-hydroxy-3-(2-phenylethyl)hexanoic acid with an optically active amine of the formula (VIII)

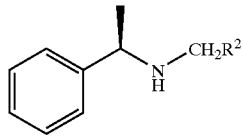

(VIII)

wherein $R^2$ is 3,4-dimethoxyphenyl or 2-chlorophenyl, using a part or the entirety left of the extraction solvent as a solvent for optical resolution.

6. The production method of claim 5, wherein the optically active amine (VIII) is produced by condensing (R)-1-phenylethylamine with a compound of the formula $R^2$—CHO (VIII-i) wherein $R^2$ is as defined above, and reducing the resulting compound.

7. The production method of claim 5, which comprises recovering the optically active amine (VIII) after optical resolution.

8. A production method of (R)-3-hydroxy-3-(2-phenylethyl)hexanoic acid, which comprises reacting magnesium, a haloacetic acid ester and 1-phenyl-3-hexanone to produce racemic 3-hydroxy-3-(2-phenylethyl)hexanoic acid ester, hydrolyzing this compound to give racemic 3-hydroxy-3-(2-phenylethyl)hexanoic acid, and optically resolving this compound using the optically active amine of the formula (VIII)

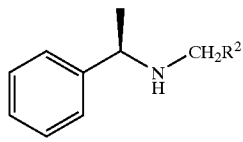

(VIII)

wherein $R^2$ is 3,4-dimethoxyphenyl or 2-chlorophenyl.

9. The production method of claim 8, wherein the haloacetic acid ester is a chloroacetic acid ester.

10. The production method of claim 8, wherein a salt of the (R)-3-hydroxy-3-(2-phenylethyl)hexanoic acid with the optically active amine (VIII) is crystallized in one or more kinds of solvents selected from ethyl acetate, methanol, isopropanol, ethanol, acetonitrile, methyl isobutyl ketone, acetone, methyl ethyl ketone, diisopropyl ether, dimethoxyethane and tetrahydrofuran, wherein the solvent optionally further contains water.

11. The production method of claim 8, wherein after producing the racemic 3-hydroxy-3-(2-phenylethyl)hexanoic acid, the compound is extracted with one or more kinds of solvents selected from ethyl acetate, methyl isobutyl ketone, methyl ethyl ketone, diisopropyl ether and tetrahydrofuran, and optically resolved by crystallizing the salt of (R)-3-hydroxy-3-(2-phenylethyl)hexanoic acid with an optically active amine (VIII) using a part or the entirety left of the extraction solvent as a solvent for optical resolution.

12. The production method of claim 8, wherein the optically active amine (VIII) is obtained by condensing (R)-1-phenylethylamine with a compound of the formula $R^2$—CHO (VIII-i) wherein $R^2$ is as defined above, and reducing the resulting compound.

13. The production method of claim 8, which comprises recovering the optically active amine (VIII) after optical resolution.

14. The production method of claim 8, wherein magnesium is activated.

15. The production method of claim 14, wherein magnesium is activated with chlorosilanes and halogenated hydrocarbon.

16. The production method of claim 15, wherein the chlorosilanes is selected from the group consisting of chlorotrimethylsilane, dichlorodimethylsilane, methyltrichlorosilane and tetrachlorosilane.

17. The production method of claim 15, wherein the halogenated hydrocarbon is selected from the group consisting of allyl bromide, iodomethane, iodoethane, benzyl bromide, 1,2-diiodoethane and 1,2-dibromoethane.

18. The production method of claim 8, wherein 1-phenyl-3-hexanone is obtained by condensing benzaldehyde with 2-pentanone in the presence of a base to give propyl styryl ketone, and reducing the obtained propyl styryl ketone.

* * * * *

UNITED STATES PATENT AND TRADEMARK OFFICE
CERTIFICATE OF CORRECTION

PATENT NO. : 6,683,207 B2
DATED : January 27, 2004
INVENTOR(S) : Tanaka et al.

It is certified that error appears in the above-identified patent and that said Letters Patent is hereby corrected as shown below:

Title Page,
Item [54], INVENTION, "(R)-3 HYDROXY-3-(2-PHENYLETHYL) HEXANOIC" should read -- (R)-3-HYDROXY-3-(2-PHENYLETHYL)HEXANOIC --.

Item [30], Foreign Application Priority Data, the following was omitted and should be added:
-- Aug. 22, 2002      (JP) ………………………………….2002-242741 --.

Signed and Sealed this

Eighth Day of June, 2004

JON W. DUDAS
*Acting Director of the United States Patent and Trademark Office*